(12) United States Patent
Gamache

(10) Patent No.: US 10,813,773 B2
(45) Date of Patent: Oct. 27, 2020

(54) REMOVABLE, BONE-SECURING COVER PLATE FOR INTERVERTEBRAL FUSION CAGE

(71) Applicant: DePuy Synthes Products, Inc., Raynham, MA (US)

(72) Inventor: Thomas Gamache, Westport, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 69 days.

(21) Appl. No.: 16/193,219

(22) Filed: Nov. 16, 2018

(65) Prior Publication Data
US 2019/0083280 A1 Mar. 21, 2019

Related U.S. Application Data

(60) Continuation of application No. 14/980,839, filed on Dec. 28, 2015, now Pat. No. 10,159,582, which is a
(Continued)

(51) Int. Cl.
*A61F 2/44* (2006.01)
*A61B 17/86* (2006.01)
*A61F 2/30* (2006.01)

(52) U.S. Cl.
CPC ............ *A61F 2/447* (2013.01); *A61F 2/442* (2013.01); *A61B 17/86* (2013.01);
(Continued)

(58) Field of Classification Search
CPC .......... A61F 2/44; A61F 2/4455; A61F 2/446; A61F 2/4465; A61F 2/447; A61B 17/7059
See application file for complete search history.

(56) References Cited

U.S. PATENT DOCUMENTS

| 1,636,636 A | 7/1927 | Humble |
| 1,677,337 A | 7/1928 | Grove |

(Continued)

FOREIGN PATENT DOCUMENTS

| CN | 201244104 | 5/2009 |
| EP | 1683490 | 7/2006 |

(Continued)

OTHER PUBLICATIONS

Allcock, "Polyphosphazenes", The Encyclopedia of Polymer Science, vol. 13, pp. 31-41, Wiley Intersciences, John Wiley & Sons, (1988).

(Continued)

*Primary Examiner* — Si Ming Ku

(57) ABSTRACT

A secondary cover plate that contacts a stand-alone fusion cage without rigidly connecting to the cage, and instead only docks against the cage (or passes through a fixation cage) and is secured into the adjacent bone. The secondary cover plate is the last item that would be added to the fixation cage construct and would at least partially cover the head of one or more angled screws. The secondary cover plate could slidably engage the fixation cage without permanently snapping into any features of the cage itself. The secondary cover plate would then be final positioned by advancing into one or more adjacent vertebral bodies. The secondary cover plate advancing step could be achieved by tapping it into place (into bone) so that it is finally secured into the bone.

1 Claim, 12 Drawing Sheets

Related U.S. Application Data division of application No. 13/235,106, filed on Sep. 16, 2011, now Pat. No. 9,248,028.

(52) U.S. Cl.
CPC . *A61F 2002/305* (2013.01); *A61F 2002/3082* (2013.01); *A61F 2002/30433* (2013.01); *A61F 2002/30471* (2013.01); *A61F 2002/30482* (2013.01); *A61F 2002/30507* (2013.01); *A61F 2002/30579* (2013.01); *A61F 2002/30593* (2013.01); *A61F 2002/30774* (2013.01); *A61F 2002/30779* (2013.01); *A61F 2002/30785* (2013.01); *A61F 2002/30787* (2013.01); *A61F 2002/30904* (2013.01); *A61F 2310/00017* (2013.01); *A61F 2310/00023* (2013.01); *A61F 2310/00029* (2013.01); *A61F 2310/0097* (2013.01); *A61F 2310/00407* (2013.01); *A61F 2310/00796* (2013.01); *A61F 2310/00976* (2013.01)

(56) References Cited

U.S. PATENT DOCUMENTS

| | | |
|---|---|---|
| 2,304,703 A | 12/1942 | O'Leary |
| 4,105,034 A | 8/1978 | Shalaby |
| 4,130,639 A | 12/1978 | Shalaby |
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,349,921 A | 9/1982 | Kuntz |
| 4,863,476 A | 9/1989 | Shepperd |
| 4,904,261 A | 2/1990 | Dove |
| 4,955,908 A | 9/1990 | Frey |
| 5,041,113 A | 8/1991 | Biedermann |
| 5,059,193 A | 10/1991 | Kuslich |
| 5,147,361 A | 9/1992 | Ojima |
| 5,209,751 A | 5/1993 | Farris |
| 5,290,312 A | 3/1994 | Kojimoto |
| 5,306,308 A | 4/1994 | Gross |
| 5,344,252 A | 9/1994 | Kakimoto |
| 5,352,231 A | 10/1994 | Brumfield |
| 5,370,697 A | 12/1994 | Baumgartner |
| 5,390,683 A | 2/1995 | Pisharodi |
| 5,391,170 A | 2/1995 | McGuire |
| 5,395,372 A | 3/1995 | Holt |
| 5,397,364 A | 3/1995 | Kozak |
| 5,443,514 A | 8/1995 | Steffee |
| 5,443,515 A | 8/1995 | Cohen |
| 5,464,407 A | 11/1995 | McGuire |
| 5,464,929 A | 11/1995 | Bezwada |
| 5,499,986 A | 3/1996 | Dimarco |
| 5,522,899 A | 6/1996 | Michelson |
| 5,529,580 A | 6/1996 | Kusunoki |
| 5,534,029 A | 7/1996 | Shima |
| 5,534,031 A | 7/1996 | Matsuzaki |
| 5,554,191 A | 9/1996 | Lahille |
| 5,591,166 A | 1/1997 | Bernhardt |
| 5,595,751 A | 1/1997 | Bezwada |
| 5,597,579 A | 1/1997 | Bezwada |
| 5,601,553 A | 2/1997 | Trebing |
| 5,607,687 A | 3/1997 | Bezwada |
| 5,609,635 A | 3/1997 | Michelson |
| 5,618,552 A | 4/1997 | Bezwada |
| 5,620,698 A | 4/1997 | Bezwada |
| 5,645,598 A | 7/1997 | Brosnahan, III |
| 5,645,850 A | 7/1997 | Bezwada |
| 5,648,088 A | 7/1997 | Bezwada |
| 5,653,763 A | 8/1997 | Errico |
| 5,658,335 A | 8/1997 | Allen |
| 5,662,655 A | 9/1997 | Laboureau |
| 5,665,122 A | 9/1997 | Kambin |
| 5,676,666 A | 10/1997 | Oxland |
| 5,697,977 A | 12/1997 | Pisharodi |
| 5,698,213 A | 12/1997 | Jamiolkowski |
| 5,700,583 A | 12/1997 | Jamiolkowski |
| 5,713,899 A | 2/1998 | Marnay |
| 5,716,415 A | 2/1998 | Steffee |
| 5,755,796 A | 5/1998 | Ibo |
| 5,772,661 A | 6/1998 | Michelson |
| 5,776,196 A | 7/1998 | Matsuzaki |
| 5,779,707 A | 7/1998 | Bertholet |
| 5,782,832 A | 7/1998 | Larsen |
| 5,785,713 A | 7/1998 | Jobe |
| 5,788,698 A | 8/1998 | Savornin |
| 5,797,912 A | 8/1998 | Runciman |
| 5,797,918 A | 8/1998 | McGuire |
| 5,800,435 A | 9/1998 | Errico |
| 5,800,440 A | 9/1998 | Stead |
| 5,859,150 A | 1/1999 | Jamiolkowski |
| 5,860,973 A | 1/1999 | Michelson |
| 5,865,848 A | 2/1999 | Baker |
| 5,888,223 A | 3/1999 | Bray, Jr. |
| 5,888,224 A | 3/1999 | Beckers |
| 5,893,889 A | 4/1999 | Harrington |
| 5,893,890 A | 4/1999 | Pisharodi |
| 5,904,689 A | 5/1999 | Jonjic |
| 5,913,860 A | 6/1999 | Scholl |
| 5,980,522 A | 11/1999 | Koros |
| 6,039,761 A | 3/2000 | Li |
| 6,045,579 A | 4/2000 | Hochshuler |
| 6,049,026 A | 4/2000 | Muschler |
| 6,056,749 A | 5/2000 | Kuslich |
| 6,066,175 A | 5/2000 | Henderson |
| 6,086,593 A | 7/2000 | Bonutti |
| 6,093,205 A | 7/2000 | McLeod |
| 6,099,531 A | 8/2000 | Bonutti |
| 6,102,950 A | 8/2000 | Vaccaro |
| 6,106,557 A | 8/2000 | Robioneck |
| 6,117,174 A | 9/2000 | Nolan |
| 6,120,503 A | 9/2000 | Michelson |
| 6,127,597 A | 10/2000 | Beyar |
| 6,129,763 A | 10/2000 | Chauvin |
| 6,139,550 A | 10/2000 | Michelson |
| 6,146,387 A | 11/2000 | Trott |
| 6,156,037 A | 12/2000 | Lehuec |
| 6,159,211 A | 12/2000 | Boriani |
| 6,176,882 B1 | 1/2001 | Biedermann |
| 6,179,794 B1 | 1/2001 | Burras |
| 6,179,873 B1 | 1/2001 | Zientek |
| 6,183,517 B1 | 2/2001 | Suddaby |
| 6,193,757 B1 | 2/2001 | Foley |
| 6,200,306 B1 | 3/2001 | Klostermeyer |
| 6,206,922 B1 | 3/2001 | Zdeblick |
| 6,231,610 B1 | 5/2001 | Geisler |
| 6,235,059 B1 | 5/2001 | Benezech |
| 6,296,647 B1 | 10/2001 | Robioneck |
| 6,302,914 B1 | 10/2001 | Michelson |
| 6,306,170 B2 | 10/2001 | Ray |
| 6,330,845 B1 | 12/2001 | Meulink |
| 6,332,895 B1 | 12/2001 | Suddaby |
| 6,336,928 B1 | 1/2002 | Guerin |
| 6,342,055 B1 | 1/2002 | Eisermann |
| 6,342,074 B1 | 1/2002 | Simpson |
| 6,364,880 B1 | 4/2002 | Michelson |
| 6,368,351 B1 | 4/2002 | Glenn |
| 6,375,462 B2 | 4/2002 | Holweg |
| 6,375,682 B1 | 4/2002 | Fleischmann |
| 6,387,130 B1 | 5/2002 | Stone |
| 6,406,478 B1 | 6/2002 | Kuo |
| 6,409,766 B1 | 6/2002 | Brett |
| 6,419,705 B1 | 7/2002 | Erickson |
| 6,419,706 B1 | 7/2002 | Graf |
| 6,423,063 B1 | 7/2002 | Bonutti |
| 6,428,575 B2 | 8/2002 | Koo |
| 6,432,106 B1 | 8/2002 | Fraser |
| 6,436,140 B1 | 8/2002 | Liu |
| 6,447,546 B1 | 9/2002 | Bramlet |
| 6,454,769 B2 | 9/2002 | Wagner |
| 6,454,806 B1 | 9/2002 | Cohen |
| 6,454,807 B1 | 9/2002 | Jackson |
| 6,461,359 B1 | 10/2002 | Tribus |

(56) References Cited

U.S. PATENT DOCUMENTS

| | | |
|---|---|---|
| 6,471,724 B2 | 10/2002 | Zdeblick |
| 6,488,710 B2 | 12/2002 | Besselink |
| 6,508,818 B2 | 1/2003 | Steiner |
| 6,527,804 B1 | 3/2003 | Gauchet |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,562,074 B2 | 5/2003 | Gerbec |
| 6,565,570 B2 | 5/2003 | Sterett |
| 6,572,619 B2 | 6/2003 | Santilli |
| 6,579,290 B1 | 6/2003 | Hardcastle |
| 6,582,468 B1 | 6/2003 | Gauchet |
| 6,602,257 B1 | 8/2003 | Thramann |
| 6,610,094 B2 | 8/2003 | Husson |
| 6,629,998 B1 | 10/2003 | Lin |
| 6,641,614 B1 | 11/2003 | Wagner |
| 6,648,917 B2 | 11/2003 | Gerbec |
| 6,676,665 B2 | 1/2004 | Foley |
| 6,682,563 B2 | 1/2004 | Scharf |
| 6,695,846 B2 | 2/2004 | Richelsoph |
| 6,706,070 B1 | 3/2004 | Wagner |
| 6,719,796 B2 | 4/2004 | Cohen |
| 6,723,126 B1 | 4/2004 | Berry |
| 6,730,125 B1 | 5/2004 | Lin |
| 6,730,127 B2 | 5/2004 | Michelson |
| 6,733,531 B1 | 5/2004 | Trieu |
| 6,733,532 B1 | 5/2004 | Gauchet |
| 6,736,850 B2 | 5/2004 | Davis |
| 6,743,255 B2 | 6/2004 | Ferree |
| 6,770,096 B2 | 8/2004 | Bolger |
| 6,773,437 B2 | 8/2004 | Ogilvie |
| 6,776,781 B1 | 8/2004 | Uwaydah |
| 6,805,714 B2 | 10/2004 | Sutcliffe |
| 6,824,564 B2 | 11/2004 | Crozet |
| 6,837,905 B1 | 1/2005 | Lieberman |
| 6,849,093 B2 * | 2/2005 | Michelson ............... A61F 2/446 623/17.15 |
| 6,855,167 B2 | 2/2005 | Shimp |
| 6,863,673 B2 | 3/2005 | Gerbec |
| 6,890,335 B2 | 5/2005 | Grabowski |
| 6,890,355 B2 | 5/2005 | Michelson |
| 6,893,464 B2 | 5/2005 | Kiester |
| 6,945,973 B2 | 9/2005 | Bray |
| 6,953,477 B2 | 10/2005 | Berry |
| 6,955,691 B2 | 10/2005 | Chae |
| 6,969,404 B2 | 11/2005 | Ferree |
| 6,969,405 B2 | 11/2005 | Suddaby |
| 6,972,019 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,018,412 B2 | 3/2006 | Ferreira |
| 7,018,416 B2 | 3/2006 | Hanson |
| 7,033,394 B2 | 4/2006 | Michelson |
| 7,037,339 B2 | 5/2006 | Houfburg |
| 7,041,135 B2 | 5/2006 | Michelson |
| 7,063,491 B2 | 6/2006 | French |
| 7,077,864 B2 | 7/2006 | Byrd, III |
| 7,083,650 B2 | 8/2006 | Moskowitz |
| 7,094,257 B2 | 8/2006 | Mujwid |
| 7,112,222 B2 | 9/2006 | Fraser |
| 7,112,223 B2 | 9/2006 | Davis |
| 7,135,024 B2 | 11/2006 | Cook |
| 7,135,043 B2 | 11/2006 | Nakahara |
| 7,163,561 B2 | 1/2007 | Michelson |
| 7,172,627 B2 | 2/2007 | Fiere |
| 7,211,112 B2 | 5/2007 | Baynham |
| 7,217,293 B2 | 5/2007 | Branch, Jr. |
| 7,220,280 B2 | 5/2007 | Kast |
| 7,223,292 B2 | 5/2007 | Messerli |
| 7,226,482 B2 | 6/2007 | Messerli |
| 7,226,483 B2 | 6/2007 | Gerber |
| 7,232,463 B2 | 6/2007 | Falahee |
| 7,232,464 B2 | 6/2007 | Mathieu |
| 7,235,101 B2 | 6/2007 | Berry |
| 7,238,203 B2 | 7/2007 | Bagga |
| 7,238,206 B2 | 7/2007 | Lange |
| 7,255,698 B2 | 8/2007 | Michelson |
| 7,276,081 B1 | 10/2007 | Coates |
| 7,288,094 B2 | 10/2007 | Lindemann |
| 7,288,095 B2 | 10/2007 | Baynham |
| 7,288,114 B2 | 10/2007 | Lange |
| 7,306,605 B2 | 12/2007 | Ross |
| 7,309,358 B2 | 12/2007 | Berry |
| 7,311,734 B2 | 12/2007 | Van Hoeck |
| 7,316,714 B2 | 1/2008 | Gordon |
| 7,323,011 B2 | 1/2008 | Shepard |
| 7,326,248 B2 | 2/2008 | Michelson |
| 7,338,525 B2 | 3/2008 | Ferree |
| 7,341,587 B2 | 3/2008 | Molz, IV |
| 7,341,590 B2 | 3/2008 | Ferree |
| 7,354,452 B2 | 4/2008 | Foley |
| 7,361,193 B2 | 4/2008 | Frey |
| 7,435,262 B2 | 10/2008 | Michelson |
| 7,438,715 B2 | 10/2008 | Doubler |
| 7,442,209 B2 | 10/2008 | Michelson |
| 7,452,370 B2 | 11/2008 | Anderson |
| 7,491,237 B2 | 2/2009 | Randall |
| 7,503,933 B2 | 3/2009 | Michelson |
| 7,507,241 B2 | 3/2009 | Levy |
| 7,527,641 B2 | 5/2009 | Suh |
| 7,569,074 B2 | 8/2009 | Eisermann |
| 7,594,931 B2 | 9/2009 | Louis |
| 7,594,932 B2 | 9/2009 | Aferzon |
| 7,601,171 B2 | 10/2009 | Ainsworth |
| 7,601,173 B2 | 10/2009 | Messerli |
| 7,608,062 B2 | 10/2009 | Sweeney |
| 7,618,456 B2 | 11/2009 | Mathieu |
| 7,618,458 B2 | 11/2009 | Biedermann |
| 7,621,950 B1 | 11/2009 | Globerman |
| 7,621,960 B2 | 11/2009 | Boyd |
| 7,628,816 B2 | 12/2009 | Magerl |
| 7,641,665 B2 | 1/2010 | Zubok |
| 7,658,766 B2 | 2/2010 | Melkent |
| 7,662,182 B2 | 2/2010 | Zubok |
| 7,674,279 B2 | 3/2010 | Johnson |
| 7,691,147 B2 | 4/2010 | Gütlin |
| 7,703,727 B2 | 4/2010 | Selness |
| 7,704,255 B2 | 4/2010 | Michelson |
| 7,722,612 B2 | 5/2010 | Sala |
| 7,722,674 B1 | 5/2010 | Grotz |
| 7,726,002 B2 | 6/2010 | Shimp |
| 7,749,270 B2 | 7/2010 | Peterman |
| 7,771,473 B2 | 8/2010 | Thramann |
| 7,785,368 B2 | 8/2010 | Schaller |
| 7,789,914 B2 | 9/2010 | Michelson |
| 7,794,502 B2 | 9/2010 | Michelson |
| 7,815,681 B2 | 10/2010 | Ferguson |
| 7,819,921 B2 | 10/2010 | Grotz |
| 7,824,445 B2 | 11/2010 | Biro |
| 7,837,734 B2 | 11/2010 | Zucherman |
| 7,846,206 B2 | 12/2010 | Oglaza |
| 7,846,207 B2 | 12/2010 | Lechmann |
| 7,850,733 B2 | 12/2010 | Baynham |
| 7,854,766 B2 | 12/2010 | Moskowitz |
| 7,862,616 B2 | 1/2011 | Lechmann |
| 7,874,980 B2 | 1/2011 | Sonnenschein |
| 7,875,062 B2 | 1/2011 | Lindemann |
| 7,875,076 B2 | 1/2011 | Mathieu |
| 7,879,098 B1 | 2/2011 | Simmons, Jr. |
| 7,883,531 B2 | 2/2011 | de Coninck |
| 7,887,589 B2 | 2/2011 | Glenn |
| 7,887,591 B2 | 2/2011 | Aebi |
| 7,887,595 B1 | 2/2011 | Pimenta |
| 7,909,870 B2 | 3/2011 | Kraus |
| 7,922,729 B2 | 4/2011 | Michelson |
| 7,951,199 B2 | 5/2011 | Miller |
| 7,985,231 B2 | 7/2011 | Sankaran |
| 7,993,403 B2 | 8/2011 | Foley |
| 8,002,808 B2 | 8/2011 | Morrison |
| 8,007,523 B2 | 8/2011 | Wagner |
| 8,021,424 B2 | 9/2011 | Beger |
| 8,021,426 B2 | 9/2011 | Segal |

(56) References Cited

U.S. PATENT DOCUMENTS

| | | |
|---|---|---|
| 8,025,697 B2 | 9/2011 | McClellan, III |
| 8,034,109 B2 | 10/2011 | Zwirkoski |
| 8,043,381 B2 | 10/2011 | Hestad |
| 8,062,375 B2 | 11/2011 | Glerum |
| 8,075,621 B2 | 12/2011 | Michelson |
| 8,177,812 B2 | 5/2012 | Sankaran |
| 8,187,329 B2 | 5/2012 | Theofilos |
| 8,192,495 B2 | 6/2012 | Simpson |
| 8,216,312 B2 | 7/2012 | Gray |
| 8,221,501 B2 | 7/2012 | Eisermann |
| 8,221,502 B2 | 7/2012 | Branch, Jr. |
| 8,231,681 B2 | 7/2012 | Castleman |
| 8,236,058 B2 | 8/2012 | Fabian |
| 8,241,358 B2 | 8/2012 | Butler |
| 8,257,442 B2 | 9/2012 | Edie |
| 8,267,939 B2 | 9/2012 | Cipoletti |
| 8,273,128 B2 | 9/2012 | Oh |
| 8,287,599 B2 | 10/2012 | McGuckin, Jr. |
| 8,303,663 B2 | 11/2012 | Jimenez |
| 8,323,345 B2 | 12/2012 | Sledge |
| 8,328,852 B2 | 12/2012 | Zehavi |
| 8,336,559 B2 | 12/2012 | Kallabat |
| 8,337,559 B2 | 12/2012 | Hansell |
| 8,343,219 B2 | 1/2013 | Allain |
| 8,349,015 B2 | 1/2013 | Bae |
| 8,353,961 B2 | 1/2013 | McClintock |
| 8,357,200 B2 | 1/2013 | Adl |
| 8,382,842 B2 | 2/2013 | Greenhalgh |
| 8,398,713 B2 | 3/2013 | Weiman |
| 8,403,990 B2 | 3/2013 | Dryer |
| 8,409,291 B2 | 4/2013 | Blackwell |
| 8,435,298 B2 | 5/2013 | Weiman |
| 8,454,617 B2 | 6/2013 | Schaller |
| 8,454,694 B2 | 6/2013 | Armstrong |
| 8,460,385 B1 | 6/2013 | Wensel |
| 8,460,387 B2 | 6/2013 | Theofilos |
| 8,470,044 B2 | 6/2013 | Bertholet |
| 8,480,747 B2 | 7/2013 | Melkent |
| 8,486,148 B2 | 7/2013 | Butler |
| 8,491,658 B1 | 7/2013 | Etminan |
| 8,491,659 B2 | 7/2013 | Weiman |
| 8,496,708 B2 | 7/2013 | Blain |
| 8,500,783 B2 | 8/2013 | Baynham |
| 8,506,635 B2 | 8/2013 | Palmatier |
| 8,518,087 B2 | 8/2013 | Lopez |
| 8,518,120 B2 | 8/2013 | Glerum |
| 8,540,769 B2 | 9/2013 | Janowski |
| 8,551,173 B2 | 10/2013 | Lechmann |
| 8,551,175 B1 | 10/2013 | Wensel |
| 8,556,979 B2 | 10/2013 | Glerum |
| 8,562,651 B2 | 10/2013 | Metcalf |
| 8,568,481 B2 | 10/2013 | Olmos |
| 8,579,977 B2 | 11/2013 | Fabian |
| 8,579,981 B2 | 11/2013 | Lim |
| 8,591,585 B2 | 11/2013 | McLaughlin |
| 8,603,170 B2 | 12/2013 | Cipoletti |
| 8,613,772 B2 | 12/2013 | Bray |
| 8,617,245 B2 | 12/2013 | Brett |
| 8,623,091 B2 | 1/2014 | Suedkamp |
| 8,628,576 B2 | 1/2014 | Triplett |
| 8,628,578 B2 | 1/2014 | Miller |
| 8,632,595 B2 | 1/2014 | Weiman |
| 8,641,765 B2 | 2/2014 | Muhanna |
| 8,663,329 B2 | 3/2014 | Ernst |
| 8,668,740 B2 | 3/2014 | Rhoda |
| 8,679,183 B2 | 3/2014 | Glerum |
| 8,685,098 B2 | 4/2014 | Glerum |
| 8,690,928 B1 | 4/2014 | Walkenhorst |
| 8,690,948 B2 | 4/2014 | Armstrong |
| 8,696,751 B2 | 4/2014 | Ashley |
| 8,709,086 B2 | 4/2014 | Glerum |
| 8,715,351 B1 | 5/2014 | Pinto |
| 8,721,723 B2 | 5/2014 | Hansell |
| 8,753,398 B2 | 6/2014 | Gordon |
| 8,758,439 B2 | 6/2014 | Linares |
| 8,764,831 B2 | 7/2014 | Lechmann |
| 8,771,360 B2 | 7/2014 | Jimenez |
| 8,778,025 B2 | 7/2014 | Ragab |
| 8,795,366 B2 | 8/2014 | Varela |
| 8,828,085 B1 | 9/2014 | Jensen |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,864,833 B2 | 10/2014 | Glerum |
| 8,888,853 B2 | 11/2014 | Glerum |
| 8,888,854 B2 | 11/2014 | Glerum |
| 8,900,307 B2 | 12/2014 | Hawkins |
| 8,926,704 B2 | 1/2015 | Glerum |
| 8,932,359 B2 | 1/2015 | Brett |
| 8,936,641 B2 | 1/2015 | Cain |
| 8,940,052 B2 | 1/2015 | Lechmann |
| 8,956,416 B2 | 2/2015 | McCarthy |
| 8,986,387 B1 | 3/2015 | To |
| 9,005,291 B2 | 4/2015 | Loebl |
| 9,005,295 B2 | 4/2015 | Kueenzi |
| 9,039,767 B2 | 5/2015 | Raymond |
| 9,039,771 B2 | 5/2015 | Glerum |
| 9,060,876 B1 | 6/2015 | To |
| 9,078,767 B1 | 7/2015 | McLean |
| 9,091,488 B2 | 7/2015 | Postma |
| 9,095,446 B2 | 8/2015 | Landry |
| 9,095,447 B2 | 8/2015 | Barreiro |
| 9,101,489 B2 | 8/2015 | Protopsaltis |
| 9,107,766 B1 | 8/2015 | McLean |
| 9,192,419 B2 | 11/2015 | McDonough |
| 9,248,028 B2 | 2/2016 | Gamache |
| 9,271,836 B2 | 3/2016 | Pavento |
| 9,278,009 B2 | 3/2016 | Bray |
| 9,292,419 B1 | 3/2016 | Kintali |
| 2002/0029044 A1 | 3/2002 | Monassevitch |
| 2002/0029082 A1 | 3/2002 | Muhanna |
| 2002/0068976 A1 | 6/2002 | Jackson |
| 2002/0068977 A1 | 6/2002 | Jackson |
| 2002/0095155 A1 | 7/2002 | Michelson |
| 2002/0128716 A1 | 9/2002 | Cohen |
| 2002/0151976 A1 | 10/2002 | Foley |
| 2002/0156475 A1 | 10/2002 | Lerch |
| 2002/0165612 A1 | 11/2002 | Gerber |
| 2003/0004575 A1 | 1/2003 | Erickson |
| 2003/0004576 A1 | 1/2003 | Thalgott |
| 2003/0023305 A1 | 1/2003 | McKay |
| 2003/0040799 A1 | 2/2003 | Boyd |
| 2003/0045940 A1 | 3/2003 | Eberlein |
| 2003/0050645 A1 | 3/2003 | Parker |
| 2003/0065396 A1 | 4/2003 | Michelson |
| 2003/0078667 A1 | 4/2003 | Manasas |
| 2003/0100949 A1 | 5/2003 | Michelson |
| 2003/0125739 A1 | 7/2003 | Bagga |
| 2003/0130739 A1 | 7/2003 | Gerbec |
| 2003/0135275 A1 | 7/2003 | Garcia |
| 2003/0139812 A1 | 7/2003 | Garcia |
| 2003/0139813 A1 | 7/2003 | Messerli |
| 2003/0153975 A1 | 8/2003 | Byrd |
| 2003/0158555 A1 | 8/2003 | Sanders |
| 2003/0187506 A1 | 10/2003 | Ross |
| 2003/0195632 A1 | 10/2003 | Foley |
| 2003/0225409 A1 | 12/2003 | Freid |
| 2003/0233145 A1 | 12/2003 | Landry |
| 2004/0024464 A1 | 2/2004 | Errico |
| 2004/0030387 A1 | 2/2004 | Landry |
| 2004/0034430 A1 | 2/2004 | Falahee |
| 2004/0064144 A1 | 4/2004 | Johnson |
| 2004/0087947 A1 | 5/2004 | Lim |
| 2004/0088055 A1 | 5/2004 | Hanson |
| 2004/0092929 A1 | 5/2004 | Zindrick |
| 2004/0111089 A1 | 6/2004 | Stevens |
| 2004/0127902 A1 | 7/2004 | Suzuki |
| 2004/0127990 A1 | 7/2004 | Bartish |
| 2004/0127991 A1 | 7/2004 | Ferree |
| 2004/0153065 A1 | 8/2004 | Lim |
| 2004/0153072 A1 | 8/2004 | Bonutti |
| 2004/0153156 A1 | 8/2004 | Cohen |
| 2004/0162618 A1 | 8/2004 | Mujwid |

(56) References Cited

U.S. PATENT DOCUMENTS

| | | |
|---|---|---|
| 2004/0172133 A1 | 9/2004 | Gerber |
| 2004/0186570 A1 | 9/2004 | Rapp |
| 2004/0186577 A1 | 9/2004 | Ferree |
| 2004/0193269 A1 | 9/2004 | Fraser |
| 2004/0199253 A1 | 10/2004 | Link |
| 2004/0199254 A1 | 10/2004 | Louis |
| 2004/0210219 A1 | 10/2004 | Bray |
| 2004/0230309 A1 | 11/2004 | DiMauro |
| 2004/0249377 A1 | 12/2004 | Kaes |
| 2004/0260286 A1 | 12/2004 | Ferree |
| 2005/0033433 A1 | 2/2005 | Michelson |
| 2005/0038513 A1 | 2/2005 | Michelson |
| 2005/0038515 A1 | 2/2005 | Kunzler |
| 2005/0065608 A1 | 3/2005 | Michelson |
| 2005/0071006 A1 | 3/2005 | Kirschman |
| 2005/0071008 A1 | 3/2005 | Kirschman |
| 2005/0085913 A1 | 4/2005 | Fraser |
| 2005/0096657 A1 | 5/2005 | Autericque |
| 2005/0101960 A1 | 5/2005 | Fiere |
| 2005/0113916 A1 | 5/2005 | Branch |
| 2005/0113917 A1 | 5/2005 | Chae |
| 2005/0125062 A1 | 6/2005 | Biedermann |
| 2005/0143749 A1 | 6/2005 | Zalenski |
| 2005/0149192 A1 | 7/2005 | Zucherman |
| 2005/0149193 A1 | 7/2005 | Zucherman |
| 2005/0154391 A1 | 7/2005 | Doherty |
| 2005/0159813 A1 | 7/2005 | Molz |
| 2005/0177236 A1 | 8/2005 | Mathieu |
| 2005/0177245 A1 | 8/2005 | Leatherbury |
| 2005/0203515 A1 | 9/2005 | Doherty |
| 2005/0222681 A1 | 10/2005 | Richley |
| 2005/0251260 A1 | 11/2005 | Gerber |
| 2005/0256576 A1 | 11/2005 | Moskowitz |
| 2005/0261769 A1 | 11/2005 | Moskowitz |
| 2005/0277938 A1 | 12/2005 | Parsons |
| 2005/0278026 A1 | 12/2005 | Gordon |
| 2006/0030851 A1 | 2/2006 | Bray |
| 2006/0058801 A1 | 3/2006 | Schlienger |
| 2006/0058876 A1 | 3/2006 | McKinley |
| 2006/0079961 A1 | 4/2006 | Michelson |
| 2006/0085071 A1 | 4/2006 | Lechmann |
| 2006/0100706 A1 | 5/2006 | Shadduck |
| 2006/0122701 A1 | 6/2006 | Kiester |
| 2006/0122703 A1 | 6/2006 | Aebi |
| 2006/0129244 A1 | 6/2006 | Ensign |
| 2006/0129424 A1 | 6/2006 | Chan |
| 2006/0136062 A1 | 6/2006 | DiNello |
| 2006/0142765 A9 | 6/2006 | Dixon |
| 2006/0142858 A1 | 6/2006 | Colleran |
| 2006/0142863 A1 | 6/2006 | Fraser |
| 2006/0178745 A1 | 8/2006 | Bartish |
| 2006/0206207 A1 | 9/2006 | Dryer |
| 2006/0229609 A1 | 10/2006 | Wang |
| 2006/0229725 A1 | 10/2006 | Lechmann |
| 2006/0235403 A1 | 10/2006 | Blain |
| 2006/0235409 A1 | 10/2006 | Blain |
| 2006/0235518 A1 | 10/2006 | Blain |
| 2006/0235531 A1 | 10/2006 | Buettner Janz |
| 2006/0235535 A1 | 10/2006 | Ferree |
| 2006/0241597 A1 | 10/2006 | Mitchell |
| 2006/0247650 A1 | 11/2006 | Yerby |
| 2006/0253201 A1 | 11/2006 | McLuen |
| 2006/0259147 A1 | 11/2006 | Krishna |
| 2006/0265075 A1 | 11/2006 | Baumgartner |
| 2006/0265077 A1 | 11/2006 | Zwirkoski |
| 2006/0293753 A1 | 12/2006 | Thramann |
| 2007/0010886 A1 | 1/2007 | Banick |
| 2007/0049941 A1 | 3/2007 | Thramann |
| 2007/0055252 A1 | 3/2007 | Blain |
| 2007/0055377 A1 | 3/2007 | Hanson |
| 2007/0106384 A1 | 5/2007 | Bray |
| 2007/0106388 A1 | 5/2007 | Michelson |
| 2007/0118222 A1 | 5/2007 | Lang |
| 2007/0129804 A1 | 6/2007 | Bentley |
| 2007/0149978 A1 | 6/2007 | Shezifi |
| 2007/0162138 A1 | 7/2007 | Heinz |
| 2007/0173939 A1 | 7/2007 | Kim |
| 2007/0191959 A1 | 8/2007 | Hartmann |
| 2007/0198016 A1 | 8/2007 | Zang |
| 2007/0198089 A1 | 8/2007 | Moskowitz |
| 2007/0208423 A1 | 9/2007 | Messerli |
| 2007/0213820 A1 | 9/2007 | Magerl |
| 2007/0219634 A1 | 9/2007 | Greenhalgh |
| 2007/0219635 A1 | 9/2007 | Mathieu |
| 2007/0233118 A1 | 10/2007 | McLain |
| 2007/0233244 A1 | 10/2007 | Lopez |
| 2007/0233253 A1 | 10/2007 | Bray |
| 2007/0233263 A1 | 10/2007 | Melkent |
| 2007/0250167 A1 | 10/2007 | Bray |
| 2007/0255416 A1 | 11/2007 | Melkent |
| 2007/0265631 A1 | 11/2007 | Fox |
| 2007/0270957 A1 | 11/2007 | Heinz |
| 2007/0270965 A1 | 11/2007 | Ferguson |
| 2007/0270968 A1 | 11/2007 | Baynham |
| 2007/0276375 A1 | 11/2007 | Rapp |
| 2007/0276490 A1 | 11/2007 | Mateyka |
| 2007/0293948 A1 | 12/2007 | Bagga |
| 2007/0299521 A1 | 12/2007 | Glenn |
| 2008/0009877 A1 | 1/2008 | Sankaran |
| 2008/0015694 A1 | 1/2008 | Tribus |
| 2008/0015701 A1 | 1/2008 | Garcia |
| 2008/0021556 A1 | 1/2008 | Edie |
| 2008/0021558 A1 | 1/2008 | Thramann |
| 2008/0027550 A1 | 1/2008 | Link |
| 2008/0033440 A1 | 2/2008 | Moskowitz |
| 2008/0051890 A1 | 2/2008 | Waugh |
| 2008/0058944 A1 | 3/2008 | Duplessis |
| 2008/0065219 A1 | 3/2008 | Dye |
| 2008/0077247 A1 | 3/2008 | Murillo |
| 2008/0082173 A1 | 4/2008 | Delurio |
| 2008/0097436 A1 | 4/2008 | Culbert |
| 2008/0103598 A1 | 5/2008 | Trudeau |
| 2008/0125865 A1 | 5/2008 | Abdelgany |
| 2008/0132949 A1 | 6/2008 | Aferzon |
| 2008/0132958 A1 | 6/2008 | Pech |
| 2008/0133012 A1 | 6/2008 | McGuckin |
| 2008/0140207 A1 | 6/2008 | Olmos |
| 2008/0147193 A1 | 6/2008 | Matthis |
| 2008/0161925 A1 | 7/2008 | Brittan |
| 2008/0167657 A1 | 7/2008 | Greenhalgh |
| 2008/0167666 A1 | 7/2008 | Fiere |
| 2008/0177307 A1 | 7/2008 | Moskowitz |
| 2008/0177388 A1 | 7/2008 | Patterson |
| 2008/0183204 A1 | 7/2008 | Greenhalgh |
| 2008/0183293 A1 | 7/2008 | Parry |
| 2008/0183294 A1 | 7/2008 | Adl |
| 2008/0195209 A1 | 8/2008 | Garcia |
| 2008/0243136 A1 | 10/2008 | Prager |
| 2008/0243251 A1 | 10/2008 | Stad |
| 2008/0243254 A1 | 10/2008 | Butler |
| 2008/0249569 A1 | 10/2008 | Waugh |
| 2008/0249575 A1 | 10/2008 | Waugh |
| 2008/0249622 A1 | 10/2008 | Gray |
| 2008/0249625 A1 | 10/2008 | Waugh |
| 2008/0255620 A1 | 10/2008 | Strauss |
| 2008/0269806 A1 | 10/2008 | Zhang |
| 2008/0281425 A1 | 11/2008 | Thalgott |
| 2008/0294262 A1 | 11/2008 | Levieux |
| 2008/0300634 A1 | 12/2008 | Gray |
| 2008/0306596 A1 | 12/2008 | Jones |
| 2008/0306598 A1 | 12/2008 | Hansen |
| 2008/0312698 A1 | 12/2008 | Bergeron |
| 2008/0312742 A1 | 12/2008 | Abernathie |
| 2009/0005873 A1 | 1/2009 | Slivka |
| 2009/0012529 A1 | 1/2009 | Blain |
| 2009/0030421 A1 | 1/2009 | Hawkins |
| 2009/0030423 A1 | 1/2009 | Puno |
| 2009/0030519 A1 | 1/2009 | Falahee |
| 2009/0030520 A1 | 1/2009 | Biedermann |
| 2009/0054991 A1 | 2/2009 | Biyani |
| 2009/0062921 A1 | 3/2009 | Michelson |
| 2009/0076610 A1 | 3/2009 | Afzal |
| 2009/0088849 A1 | 4/2009 | Armstrong |
| 2009/0099554 A1 | 4/2009 | Forster |

(56) References Cited

U.S. PATENT DOCUMENTS

| | | |
|---|---|---|
| 2009/0099568 A1 | 4/2009 | Lowry |
| 2009/0105771 A1 | 4/2009 | Lei |
| 2009/0105774 A1 | 4/2009 | Jones |
| 2009/0105830 A1 | 4/2009 | Jones |
| 2009/0105831 A1 | 4/2009 | Jones |
| 2009/0112320 A1 | 4/2009 | Kraus |
| 2009/0112324 A1 | 4/2009 | Refai |
| 2009/0125028 A1 | 5/2009 | Teisen |
| 2009/0131988 A1 | 5/2009 | Bush, Jr. |
| 2009/0132054 A1 | 5/2009 | Zeegers |
| 2009/0143859 A1 | 6/2009 | McClellan, III |
| 2009/0164020 A1 | 6/2009 | Janowski |
| 2009/0182428 A1 | 7/2009 | McClellan, III |
| 2009/0182430 A1 | 7/2009 | Tyber |
| 2009/0192549 A1 | 7/2009 | Sanders |
| 2009/0192613 A1 | 7/2009 | Wing |
| 2009/0192615 A1 | 7/2009 | Tyber |
| 2009/0192616 A1 | 7/2009 | Zielinski |
| 2009/0198245 A1 | 8/2009 | Phan |
| 2009/0198287 A1 | 8/2009 | Chiu |
| 2009/0210062 A1 | 8/2009 | Thalgott |
| 2009/0210064 A1 | 8/2009 | Lechmann |
| 2009/0222096 A1 | 9/2009 | Trieu |
| 2009/0222099 A1 | 9/2009 | Liu |
| 2009/0234398 A1 | 9/2009 | Chirico |
| 2009/0240335 A1 | 9/2009 | Arcenio |
| 2009/0248159 A1 | 10/2009 | Aflatoon |
| 2009/0265007 A1 | 10/2009 | Colleran |
| 2009/0287251 A1 | 11/2009 | Bae |
| 2009/0292361 A1 | 11/2009 | Lopez |
| 2009/0306779 A1 | 12/2009 | Ahn |
| 2009/0326580 A1 | 12/2009 | Anderson |
| 2009/0326589 A1 | 12/2009 | Lemoine |
| 2010/0004747 A1 | 1/2010 | Lin |
| 2010/0016901 A1 | 1/2010 | Robinson |
| 2010/0016905 A1 | 1/2010 | Greenhalgh |
| 2010/0023128 A1 | 1/2010 | Malberg |
| 2010/0030334 A1 | 2/2010 | Molz, IV |
| 2010/0036496 A1 | 2/2010 | Yu |
| 2010/0042159 A1 | 2/2010 | Butler |
| 2010/0057206 A1 | 3/2010 | Duffield |
| 2010/0070037 A1 | 3/2010 | Parry |
| 2010/0087925 A1 | 4/2010 | Kostuik |
| 2010/0106249 A1 | 4/2010 | Tyber |
| 2010/0145457 A1 | 6/2010 | Felt |
| 2010/0145459 A1 | 6/2010 | McDonough |
| 2010/0145460 A1 | 6/2010 | McDonough |
| 2010/0179594 A1 | 7/2010 | Theofilos |
| 2010/0185289 A1 | 7/2010 | Kirwan |
| 2010/0204739 A1 | 8/2010 | Bae |
| 2010/0204795 A1 | 8/2010 | Greenhalgh |
| 2010/0217325 A1 | 8/2010 | Hochschuler |
| 2010/0217393 A1 | 8/2010 | Theofilos |
| 2010/0234956 A1 | 9/2010 | Attia |
| 2010/0249935 A1 | 9/2010 | Slivka |
| 2010/0249937 A1 | 9/2010 | Blain |
| 2010/0262240 A1 | 10/2010 | Chavatte |
| 2010/0286777 A1 | 11/2010 | Errico |
| 2010/0286781 A1 | 11/2010 | Bullard |
| 2010/0286783 A1 | 11/2010 | Lechmann |
| 2010/0292696 A1 | 11/2010 | Chantelot |
| 2010/0292737 A1 | 11/2010 | Suh |
| 2010/0305704 A1 | 12/2010 | Messerli |
| 2010/0312345 A1 | 12/2010 | Duffield |
| 2010/0324607 A1 | 12/2010 | Davis |
| 2011/0004308 A1 | 1/2011 | Marino |
| 2011/0004310 A1 | 1/2011 | Michelson |
| 2011/0009908 A1 | 1/2011 | Ferguson |
| 2011/0009966 A1 | 1/2011 | Michelson |
| 2011/0015675 A1 | 1/2011 | Howard |
| 2011/0015745 A1 | 1/2011 | Bucci |
| 2011/0015747 A1 | 1/2011 | McManus |
| 2011/0029082 A1 | 2/2011 | Hall |
| 2011/0035011 A1 | 2/2011 | Cain |
| 2011/0082550 A1 | 4/2011 | Yeh |
| 2011/0082555 A1 | 4/2011 | Martz |
| 2011/0093074 A1 | 4/2011 | Glerum |
| 2011/0098747 A1 | 4/2011 | Donner |
| 2011/0106159 A1 | 5/2011 | Nazeck |
| 2011/0118843 A1 | 5/2011 | Mathieu |
| 2011/0130835 A1 | 6/2011 | Ashley |
| 2011/0130838 A1 | 6/2011 | Morgenstern Lopez |
| 2011/0144703 A1 | 6/2011 | Krause |
| 2011/0144753 A1 | 6/2011 | Marchek |
| 2011/0172716 A1 | 7/2011 | Glerum |
| 2011/0184415 A1 | 7/2011 | Anderson |
| 2011/0185292 A1 | 7/2011 | Chawla |
| 2011/0190892 A1 | 8/2011 | Kirschman |
| 2011/0202136 A1 | 8/2011 | Brittan |
| 2011/0208311 A1 | 8/2011 | Janowski |
| 2011/0213421 A1 | 9/2011 | Binder |
| 2011/0230971 A1 | 9/2011 | Donner |
| 2011/0251689 A1 | 10/2011 | Seifert |
| 2011/0270261 A1 | 11/2011 | Mast |
| 2011/0282453 A1 | 11/2011 | Greenhalgh |
| 2011/0301711 A1 | 12/2011 | Palmatier |
| 2011/0301712 A1 | 12/2011 | Palmatier |
| 2011/0319898 A1 | 12/2011 | O'Neil |
| 2011/0319998 A1 | 12/2011 | O'Neil |
| 2012/0004726 A1 | 1/2012 | Greenhalgh |
| 2012/0004732 A1 | 1/2012 | Goel |
| 2012/0022654 A1 | 1/2012 | Farris |
| 2012/0029636 A1 | 2/2012 | Ragab |
| 2012/0041559 A1 | 2/2012 | Melkent |
| 2012/0071977 A1 | 3/2012 | Oglaza |
| 2012/0071980 A1 | 3/2012 | Purcell |
| 2012/0078371 A1 | 3/2012 | Gamache |
| 2012/0078372 A1 | 3/2012 | Gamache |
| 2012/0078373 A1 | 3/2012 | Gamache |
| 2012/0083889 A1 | 4/2012 | Purcell |
| 2012/0101581 A1 | 4/2012 | Mathieu |
| 2012/0109309 A1 | 5/2012 | Mathieu |
| 2012/0109310 A1 | 5/2012 | Mathieu |
| 2012/0109311 A1 | 5/2012 | Mathieu |
| 2012/0109312 A1 | 5/2012 | Mathieu |
| 2012/0109313 A1 | 5/2012 | Mathieu |
| 2012/0123546 A1 | 5/2012 | Medina |
| 2012/0150301 A1 | 6/2012 | Gamache |
| 2012/0150303 A1 | 6/2012 | Linares |
| 2012/0158143 A1 | 6/2012 | Shapiro |
| 2012/0185049 A1 | 7/2012 | Varela |
| 2012/0197401 A1 | 8/2012 | Duncan |
| 2012/0197403 A1 | 8/2012 | Merves |
| 2012/0197405 A1 | 8/2012 | Cuevas |
| 2012/0203230 A1 | 8/2012 | Adams |
| 2012/0209331 A1 | 8/2012 | Michelson |
| 2012/0226319 A1 | 9/2012 | Armstrong |
| 2012/0226357 A1 | 9/2012 | Varela |
| 2012/0290097 A1 | 11/2012 | Cipoletti |
| 2012/0310350 A1 | 12/2012 | Farris |
| 2012/0310352 A1 | 12/2012 | DiMauro |
| 2013/0030536 A1 | 1/2013 | Rhoda |
| 2013/0060337 A1 | 3/2013 | Petersheim |
| 2013/0073044 A1 | 3/2013 | Gamache |
| 2013/0085572 A1 | 4/2013 | Glerum |
| 2013/0085574 A1 | 4/2013 | Sledge |
| 2013/0116791 A1 | 5/2013 | Theofilos |
| 2013/0123924 A1 | 5/2013 | Butler |
| 2013/0123927 A1 | 5/2013 | Malandain |
| 2013/0138214 A1 | 5/2013 | Greenhalgh |
| 2013/0144387 A1 | 6/2013 | Walker |
| 2013/0144388 A1 | 6/2013 | Emery |
| 2013/0158663 A1 | 6/2013 | Miller |
| 2013/0158664 A1 | 6/2013 | Palmatier |
| 2013/0158667 A1 | 6/2013 | Tabor |
| 2013/0158668 A1 | 6/2013 | Nichols |
| 2013/0158669 A1 | 6/2013 | Sungarian |
| 2013/0166027 A1 | 6/2013 | Bellas |
| 2013/0173004 A1 | 7/2013 | Greenhalgh |
| 2013/0190876 A1 | 7/2013 | Drochner |
| 2013/0190877 A1 | 7/2013 | Medina |
| 2013/0204371 A1 | 8/2013 | McLuen |
| 2013/0211525 A1 | 8/2013 | McLuen |
| 2013/0211526 A1 | 8/2013 | Alheidt |

(56) References Cited

U.S. PATENT DOCUMENTS

| | | |
|---|---|---|
| 2013/0238095 A1 | 9/2013 | Pavento |
| 2013/0268080 A1 | 10/2013 | Melkent |
| 2013/0310939 A1 | 11/2013 | Fabian |
| 2013/0325071 A1 | 12/2013 | Niemiec |
| 2013/0345813 A1 | 12/2013 | Frank |
| 2014/0025169 A1 | 1/2014 | Lechmann |
| 2014/0039622 A1 | 2/2014 | Glerum |
| 2014/0039623 A1 | 2/2014 | Iott |
| 2014/0046333 A1 | 2/2014 | Johnson |
| 2014/0058513 A1 | 2/2014 | Gahman |
| 2014/0067073 A1 | 3/2014 | Hauck |
| 2014/0107786 A1 | 4/2014 | Geisler |
| 2014/0114415 A1 | 4/2014 | Tyber |
| 2014/0114423 A1 | 4/2014 | Suedkamp |
| 2014/0128977 A1 | 5/2014 | Glerum |
| 2014/0135930 A1 | 5/2014 | Georges |
| 2014/0135934 A1 | 5/2014 | Hansell |
| 2014/0142705 A1 | 5/2014 | Duffield |
| 2014/0142706 A1 | 5/2014 | Hansell |
| 2014/0156009 A1 | 6/2014 | Armstrong |
| 2014/0163683 A1 | 6/2014 | Seifert |
| 2014/0172103 A1 | 6/2014 | O'Neil |
| 2014/0172106 A1 | 6/2014 | To |
| 2014/0180421 A1 | 6/2014 | Glerum |
| 2014/0228959 A1 | 8/2014 | Niemiec |
| 2014/0243981 A1 | 8/2014 | Davenport |
| 2014/0243982 A1 | 8/2014 | Miller |
| 2014/0249629 A1 | 9/2014 | Moskowitz |
| 2014/0249630 A1 | 9/2014 | Weiman |
| 2014/0257484 A1 | 9/2014 | Flower |
| 2014/0257486 A1 | 9/2014 | Alheidt |
| 2014/0277474 A1 | 9/2014 | Robinson |
| 2014/0303731 A1 | 10/2014 | Glerum |
| 2014/0303732 A1 | 10/2014 | Rhoda |
| 2014/0324171 A1 | 10/2014 | Glerum |
| 2015/0012097 A1 | 1/2015 | Ibarra |
| 2015/0045894 A1 | 2/2015 | Hawkins |
| 2015/0094812 A1 | 4/2015 | Cain |
| 2015/0094813 A1 | 4/2015 | Lechmann |
| 2015/0112438 A1 | 4/2015 | McLean |
| 2015/0182347 A1 | 7/2015 | Robinson |
| 2015/0250606 A1 | 9/2015 | McLean |
| 2015/0257892 A1 | 9/2015 | Lechmann |
| 2015/0374511 A1 | 12/2015 | Pavento |
| 2016/0213487 A1 | 7/2016 | Wilson |

FOREIGN PATENT DOCUMENTS

| | | |
|---|---|---|
| EP | 1774926 | 4/2007 |
| GB | G220729 | 1/1990 |
| GB | G457673 | 8/2009 |
| WO | WO 1998004217 | 2/1998 |
| WO | WO 1999038463 | 8/1999 |
| WO | WO 1999052473 | 10/1999 |
| WO | WO 2001008864 | 2/2001 |
| WO | WO 2002013732 | 2/2002 |
| WO | WO 2003005939 | 5/2003 |
| WO | WO 2003090650 | 11/2003 |
| WO | WO 2004069106 | 8/2004 |
| WO | WO 2003070128 | 10/2004 |
| WO | WO 2005020861 | 3/2005 |
| WO | WO 2006084057 | 8/2006 |
| WO | WO 2007003785 | 1/2007 |
| WO | WO 2007118856 | 10/2007 |
| WO | WO 2007098288 | 3/2008 |
| WO | WO 2009025841 | 2/2009 |
| WO | WO 2008149223 | 4/2009 |
| WO | WO 2009064644 | 5/2009 |
| WO | WO 2009091775 | 9/2009 |
| WO | WO 2009136009 | 11/2009 |
| WO | WO 2010028045 | 3/2010 |
| WO | WO 2010054208 | 5/2010 |
| WO | WO 2010092893 | 8/2010 |
| WO | WO 2010099239 | 9/2010 |
| WO | WO 2010121028 | 12/2010 |
| WO | WO 2011008864 | 1/2011 |
| WO | WO 2011080535 | 7/2011 |
| WO | WO 2012056119 | 5/2012 |
| WO | WO 2013018062 | 2/2013 |
| WO | WO 2013096192 | 6/2013 |
| WO | WO 2013191979 | 12/2013 |

OTHER PUBLICATIONS

Cain, "New Stand-Alone Anterior Lumbar Interbody Fusion Device: Bioemechanical Comparison with Established Fixation Techniques", Spine, vol. 30, No. 23, pp. 2631-2636, 2005, Lippincott Williams & Wilkins Inc.

Cohn and Younes, "Biodegradable PEO/PLA Block Copolymers", Journal of Biomaterials Research, 1988, vol. 22, pp. 993-1009.

Cohn, "Polymer Preprints", ACS Division of Polymer Chemistry, vol. 30(1), 1989, p. 498, (e.g. PEO/PLA).

Gercek, "Subsidence of Stand-Alone Cervical Cages in Anterior Interbody Fusion: Warning", Eur Spine J., vol. 12, pp. 513-516, 2003, Springer-Verlag.

Heller, "Poly(Ortho Esters)", Handbook of Biodegradable Polymers, edited by Domb, et al, Hardwood Academic Press, pp. 99-118, 1997.

Humphries, "Anterior Fusion of the Lumbar Spine Using an Internal Fixative Device", Surgical Forum, vol. IX, pp. 770-773, American College of Surgeons, 1959, Chicago Illinois.

Kandziora, "Biomechanical Comparison of Cervical Spine Interbody Fusion Cages", Spine, vol. 26, No. 17, pp. 1850-1857, 2001, Lippincott Williams & Wilkins, Inc.

Kemnitzer and Kohn, "Degradable Polymers Derived From the Amino Acid L-Tyrosine", The Handbook of Biodegradable Polymers, edited by Domb, et. al., Hardwood Academic Press, 1997, pp. 251-272.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Pavlov, "Good Outcome and Restoration of Lordosis After Anterior Lumbar Interbody Fusion With Additional Posterior Fixation", Spine, vol. 29, No. 17, pp. 1893-1900, 2004, Lippincott Williams & Wilkins.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Vandorpe, "Biodegradable Polyphosphazenes for Biomeidcal Applications", The Handbook of Biodegradable Polymers, edited by Domb, et al, Hardwood Academic Press, 1997, pp. 161-182.

Pederson, "Thermal Assembly of a Biomimetic Mineral/Collagen Composite", Biomaterials, 2003, vol. 2, pp. 4881-4890, Elsevier.

\* cited by examiner

REMOVABLE, BONE-SECURING COVER PLATE FOR INTERVERTEBRAL FUSION CAGE

CONTINUING DATA

This application is a continuation application claiming priority from patent application U.S. Ser. No. 14/980,839, filed Dec. 28, 2015, entitled "Removable, Bone-Securing Cover Plate for Intervertebral Fusion Cage" (Gamache), Docket Number DEP6426USDIV1, and U.S. Ser. No. 13/235,106, filed Sep. 16, 2011, entitled "Removable, Bone-Securing Cover Plate for Intervertebral Fusion Cage" (Gamache), Docket Number DEP6426USNP (now U.S. Pat. No. 9,248,028), the specifications of which are incorporated by reference in their entireties.

BACKGROUND OF THE INVENTION

A stand-alone fusion cage is a fusion cage that has at least one angled hole in its anterior face for receiving a bone screw that passes through the cage an into an adjacent vertebral body. There are numerous conventional embodiments of these cages that capture the angled bone-engaging screw so as to ensure that the screw does not back out of the cage. Some of the known anti-backout mechanisms include: assembled rotating cover plates, cams, bushings, expanding screws, set screws and secondary cover plates that either snap onto the cage itself or are docked to the cage and secured to the cage faceplate using additional hardware such as a screw. These secondary cover plates can fully or partially cover the most proximal (anterior) portion of the screw head and would in theory prevent any screw backouts.

The following references are pertinent to the field of stand-alone cages: US 2008-0027550 (Link); US2010-0057206; U.S. Pat. No. 6,730,127; US2009-0088849; US2010-0145459; U.S. Pat. Nos. 7,662,182; 6,972,019; US2008-0249569; US2009-0105831; U.S. Pat. Nos. 7,306,605; 7,288,094; US2010-0312345; US2010-0286777; U.S. Pat. No. 6,945,973; US2010-0106249; U.S. Pat. Nos. 6,849,093; 6,984,234; US2009-0105830; US2009-0210062; U.S. Pat. Nos. 7,452,370; 6,558,423; 6,890,335; and 6,629,998.

SUMMARY OF THE INVENTION

The present invention relates to a secondary cover plate that engages a stand-alone intervertebral fusion cage without rigidly connecting to the cage. Rather, the cover plate of the present invention only docks against or passes through the cage and is secured into the adjacent bone.

The secondary cover plate of the present invention is typically the last component of the intervertebral fusion assembly that is inserted into the disc space. Typically, its primary function is to at least partially cover the head of one or more angled screws.

In some embodiments, the secondary cover plate of the present invention slidably engages the fixation cage without permanently snapping into any features of the cage component. In other embodiments, the secondary cover plate threadably engages the cage without permanently snapping into any features of the cage.

After this removable engagement, the secondary cover plate is then secured into its final position by advancing into one or more adjacent vertebral bodies. This advancing step may be achieved by tapping its bone-securement features into the adjacent bones or rotating these bone securement features into the adjacent bone, so that the cover plate is finally secured into the bone.

Therefore, in accordance with the present invention, there is provided an assembly comprising:
a) an intervertebral fusion cage positionable between adjacent vertebral bodies, the cage having an anterior face having a pair of anchor holes extending therethrough,
b) bone anchors received in the anchor holes, each anchor having a proximal head,
c) a cover plate having:
i) a base portion having an anterior face and a posterior face,
ii) opposed bone-securing features extending from the base portion,
wherein the cover plate is removably connected to the cage.

DETAILED DESCRIPTION OF THE INVENTION

Figure 3:
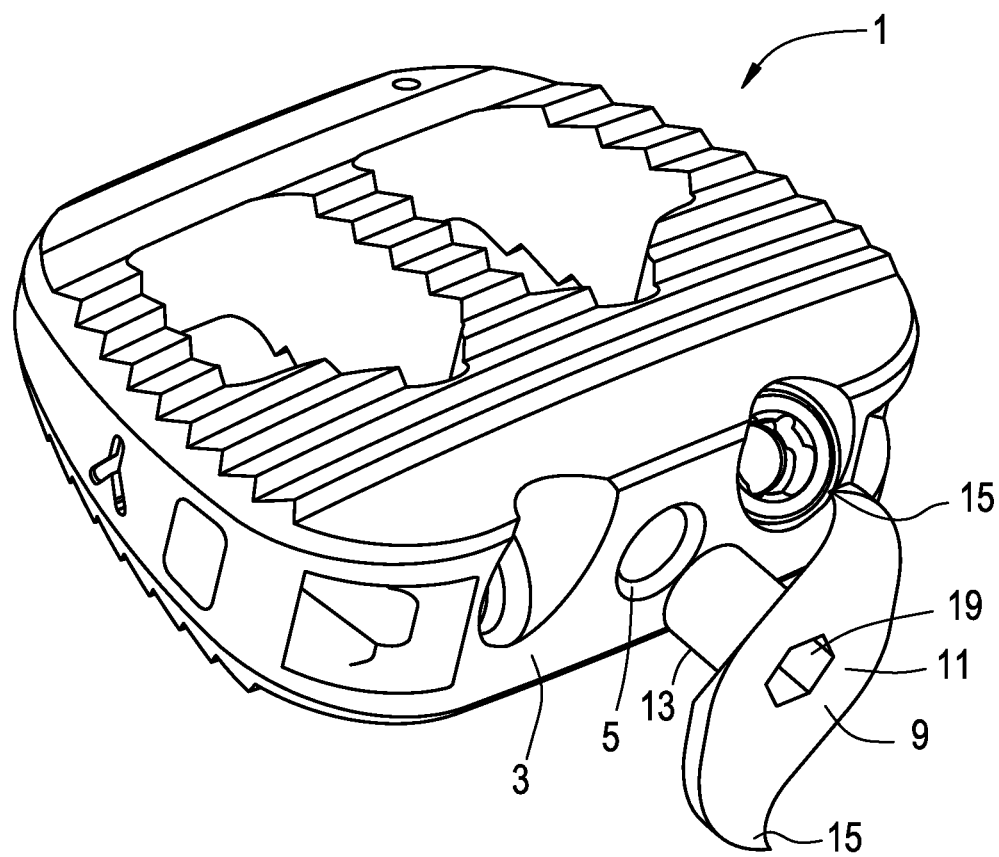
FIG. 3 discloses an exploded version of a second embodiment of the present invention (without screws) having a smooth post, wherein the bone-securing features are in deployed position.

Now referring to FIGS. 1A-B, 2A-B, 3 and 6, there is provided an assembly comprising:

a) an intervertebral fusion cage 1 positionable between adjacent vertebral bodies, the cage having an anterior face 3 having a receptacle 5 and a pair of anchor holes 901, and
b) a cover plate 7 having:
   i) a base portion 9 having an anterior face 11 and a posterior face (not shown),
   ii) a post 13 extending from the posterior face of the base portion and removably engaged in the receptacle of the cage, and
   iii) opposed bone-securing features 15 for engaging the adjacent vertebral bodies
c) bone anchors 903 received in the anchor holes, each anchor having a proximal head 905, and In some embodiments, as in FIG. 3, the shaft and receptacle each have mating circular transverse cross-sections so that the shaft is rotatable with the receptacle.

Figure 1A:
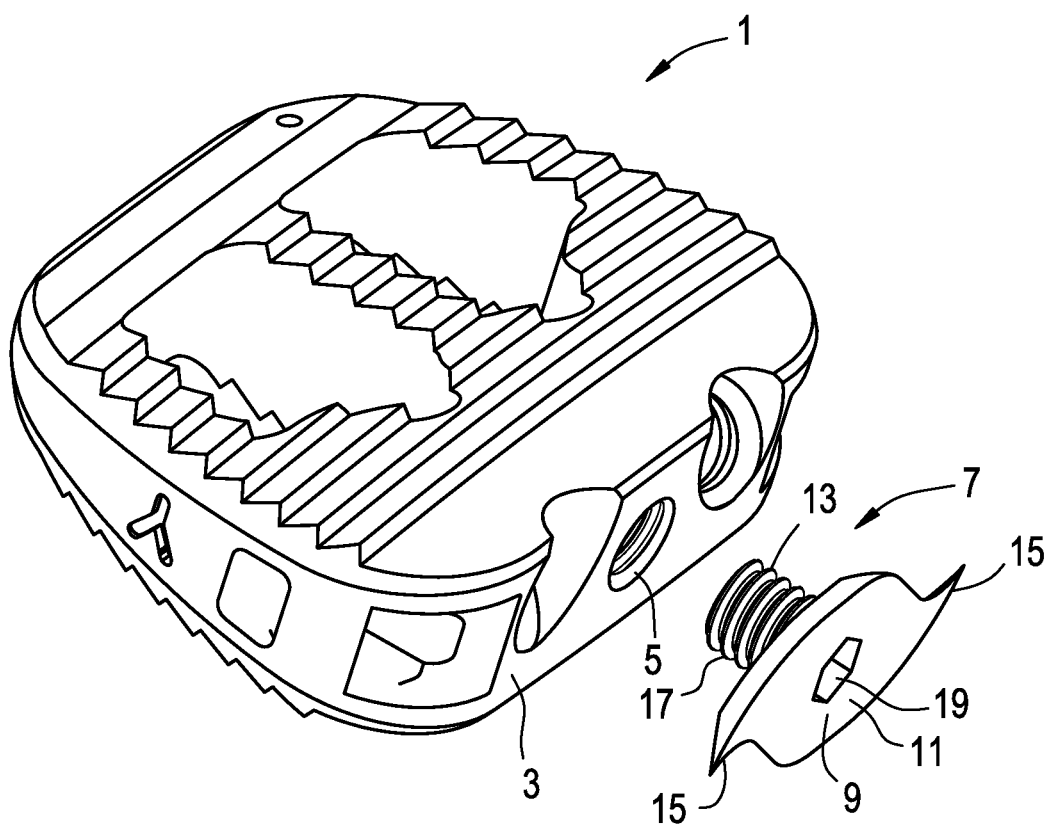
FIG. 1A discloses an exploded version of a first embodiment of the present invention (without screws) having a threaded post, wherein the bone-securing features are not in deployed position.
Figure 1B:
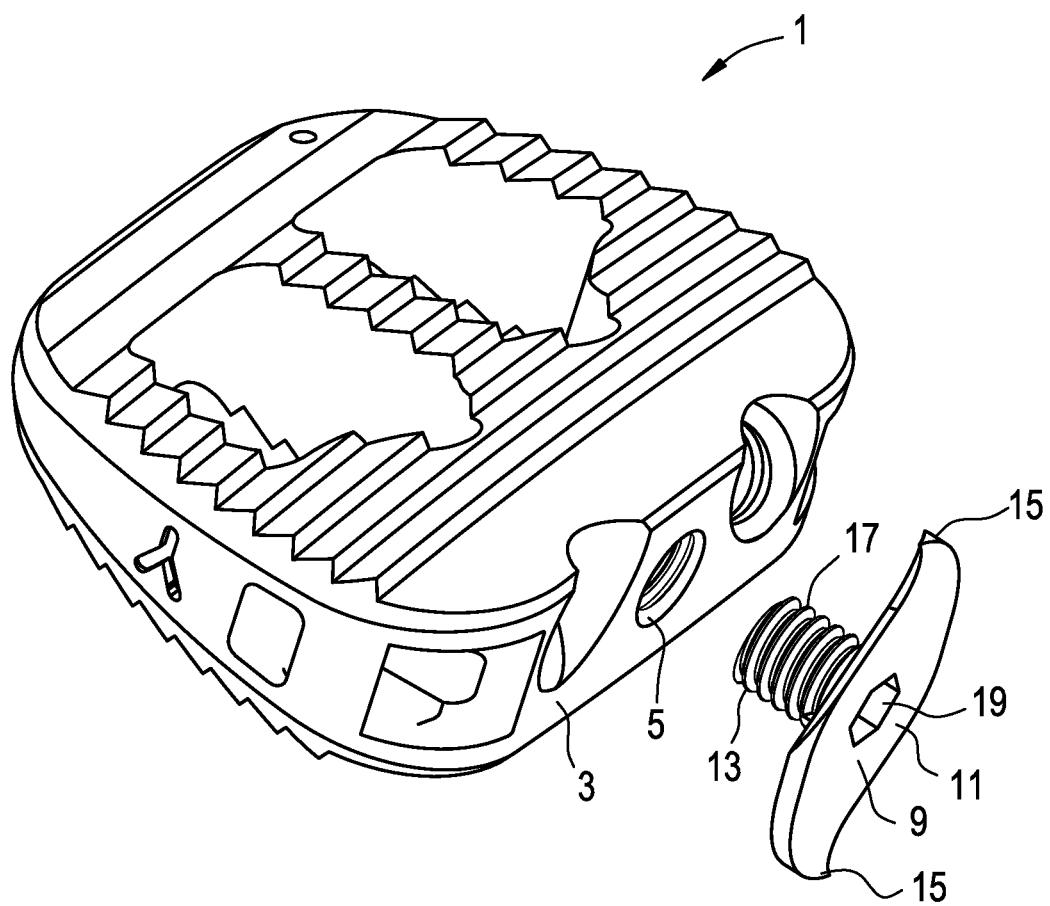
FIG. 1B discloses an exploded version of a first embodiment of the present invention (without screws) having a threaded post, wherein the bone-securing features are in deployed position.
Figure 2A:
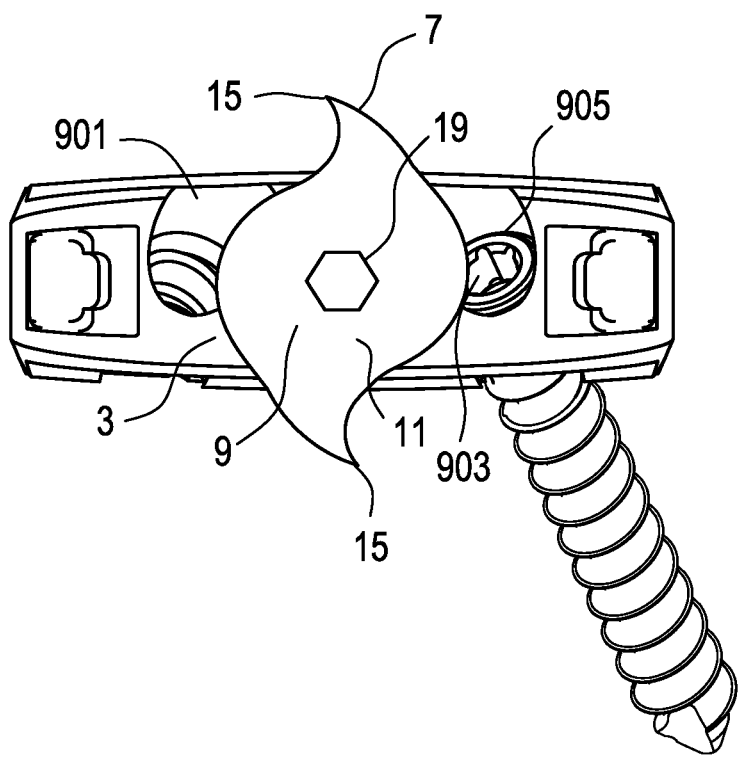
FIGS. 2A and 2B are side and top views of the assembled first embodiment of the present invention.
Figure 2B:
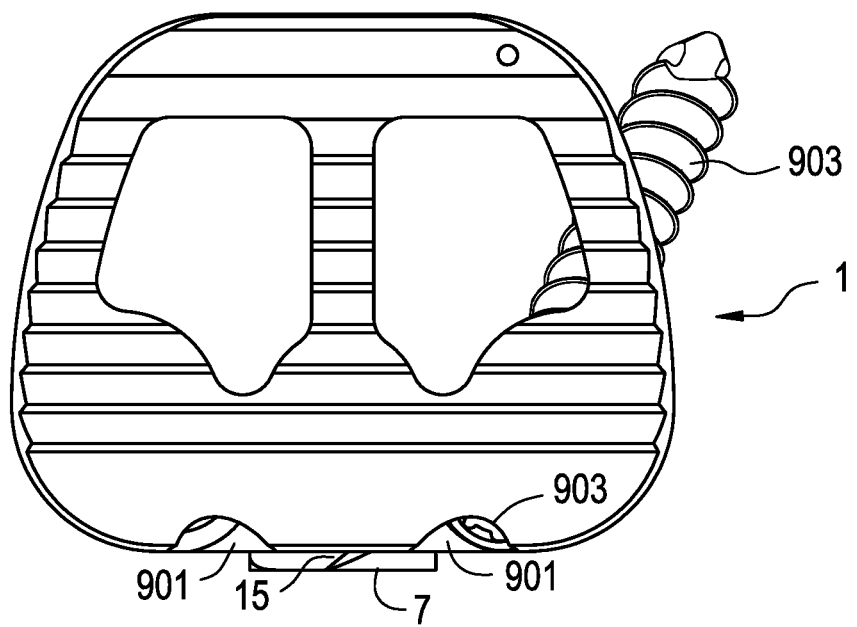

In some embodiments, as in FIG. 1A, the shaft has a threadform 17 thereon, where in other, as in FIG. 3, the shaft is unthreaded.

In some embodiments, as in FIG. 3, the bone-securing features are integral with the base portion. In others, the bone-securing features are rotatable about the base portion, as in FIG. 9.

Typically, the cover plate further comprises a recess 19 opening upon the anterior face of the base portion. Preferably, this opening has a hexagonal transverse cross-section.

In some embodiments, as in FIGS. 1A and 3, the bone-securing features extend laterally from the base portion and the shaft is rotatable with the receptacle.

Figure 6:
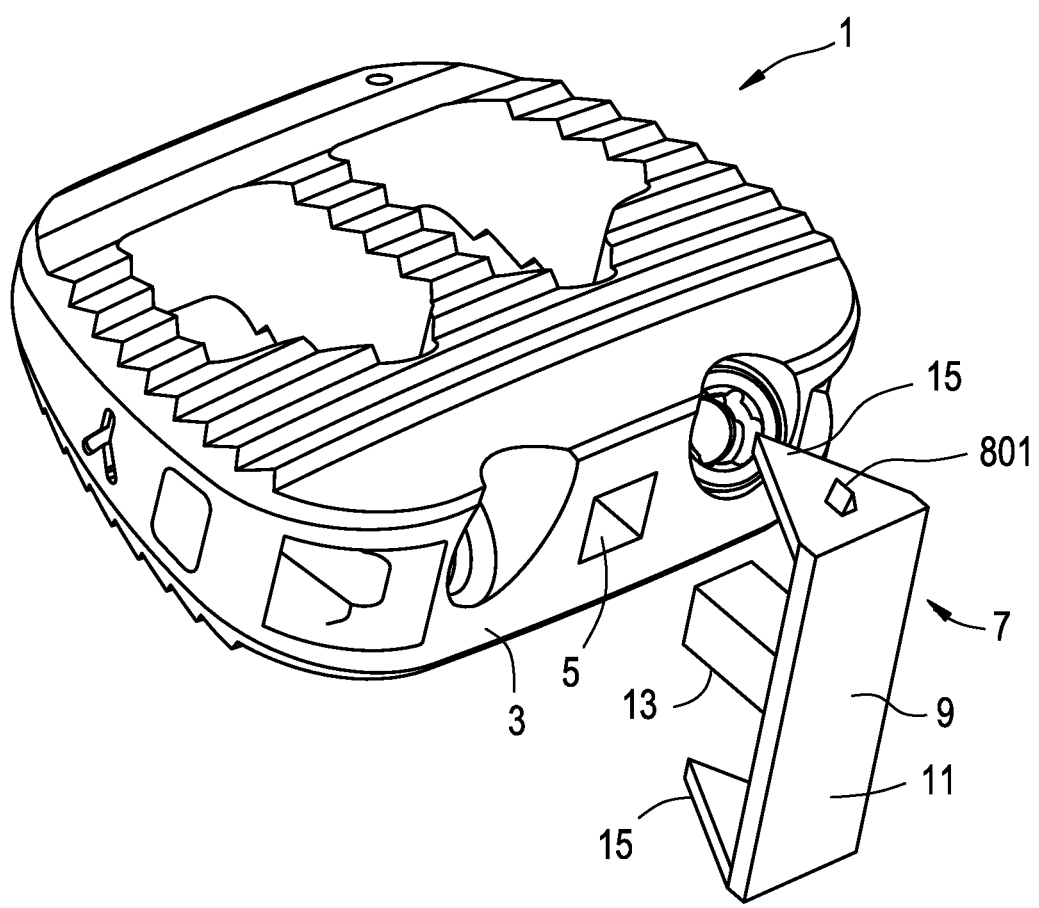
FIG. 6 discloses an exploded version of a fifth embodiment of the present invention (without screws) having a smooth rectangular post and opposed bone-securing features.

In some embodiments, as in FIG. 6, the bone-securing features extend posteriorly from the base portion.

Figure 7:
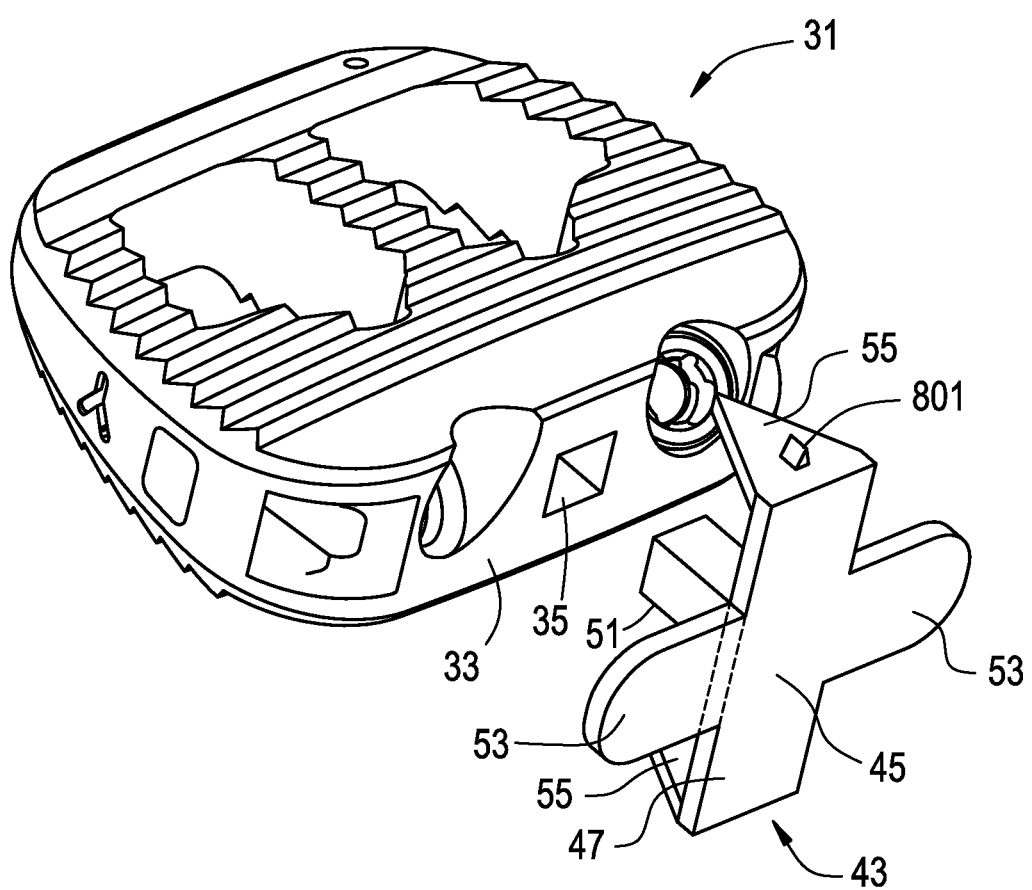
FIG. 7 discloses an exploded version of a sixth embodiment of the present invention (without screws) having a smooth rectangular post; opposed bone-securing features; and lateral flanges.

In some embodiments, as in FIGS. 6 and 7, the bone-securing features comprise an anti-backout feature 801.

The base portion of the cover plate acts as a hub for the other features of the cover plate.

The recess that opens upon the anterior face of the base portion of the cover plate functions as a receptacle for a tool that is able to rotate the cover plate. In some preferred embodiments, this recess has a hexagonal transverse cross-section, so as to be useful with standard hexagonal scewdrivers.

The purpose of the post to to provide a removable engagement of the cover plate to the cage. Accordingly, the post does not preferably possess any features that would provide a permanent engagement between the cover plate and the cage, such as a snap feature.

In some embodiments the post has a smooth outer surface, as in FIG. 3. This surface is usually adopted when the bone-securement features are tapped into the bone.

In some embodiments the post has a threaded outer surface, as in FIG. 1A. This threaded surface is usually adopted when the bone-securement features are rotated into the bone.

In some embodiments the post has a circular transverse cross-section, as in FIG. 1A. This threaded surface may be usefully adopted when the bone-securement features are rotated into the bone.

In some embodiments the post has a rectangular transverse cross-section, as in FIG. 6. This surface is usually adopted when the bone-securement features are tapped into the bone. The non-circular cross section of the post provides for auto-alignment of the cover plate.

Figure 4A:
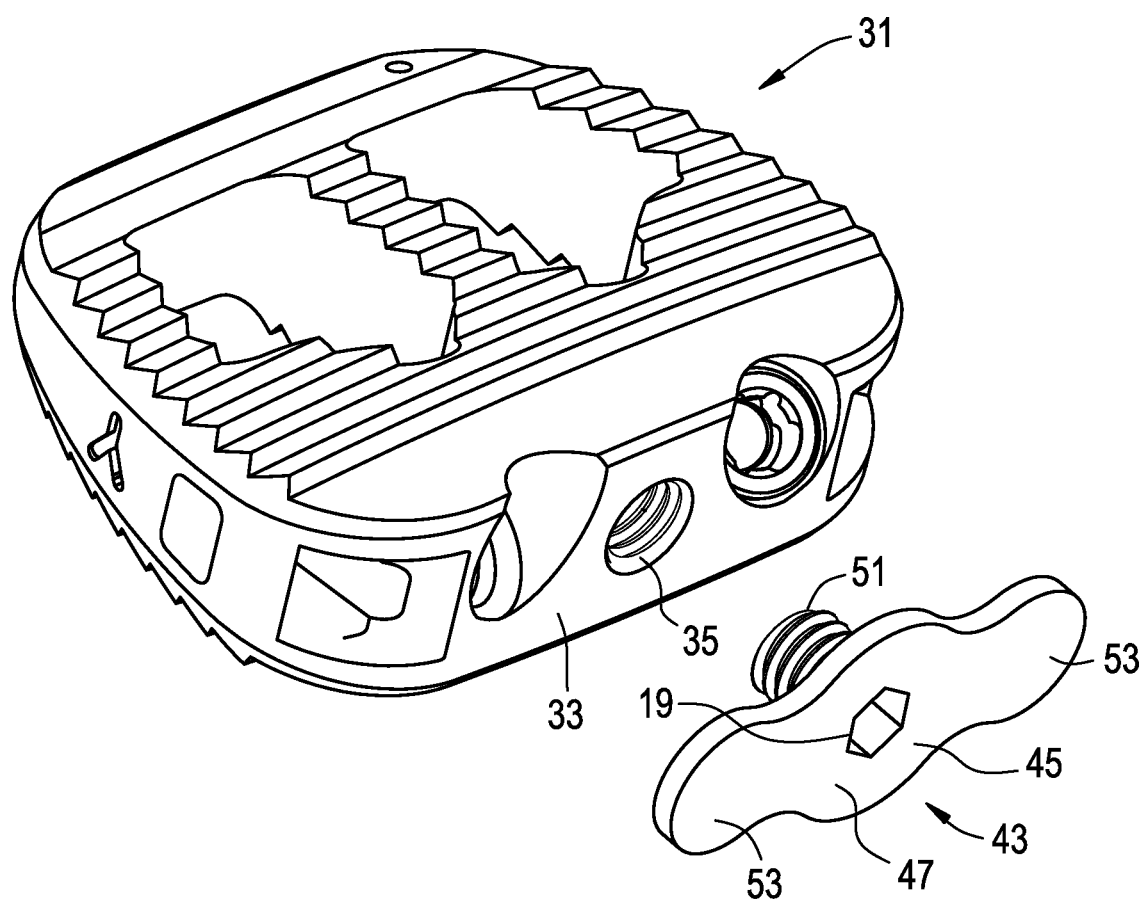
FIG. 4A discloses an exploded version of a third embodiment of the present invention (without screws) having a threaded post and lateral flanges.
Figure 4B:
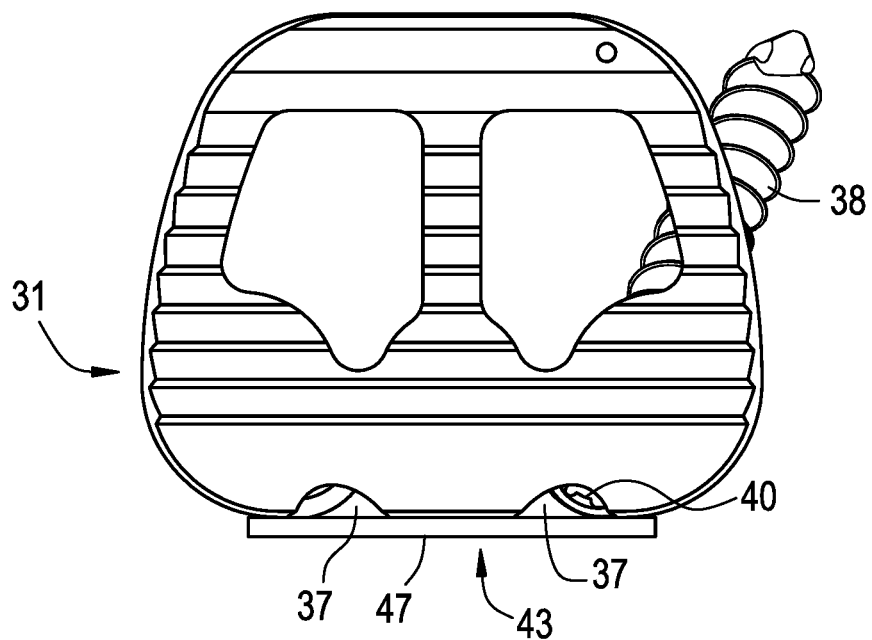
FIGS. 4B and 4C are side and top views of the assembled first embodiment of the present invention.
Figure 4C:
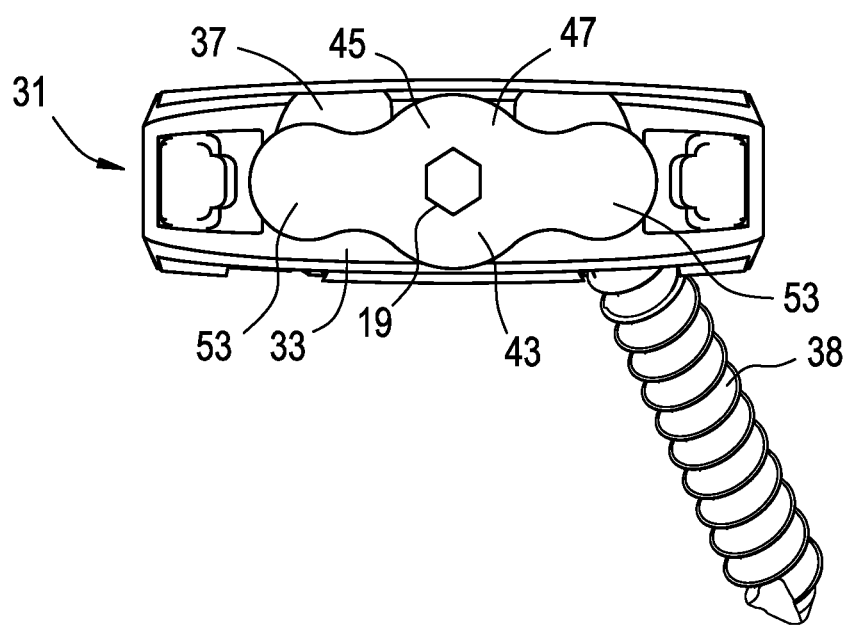
Figure 5:
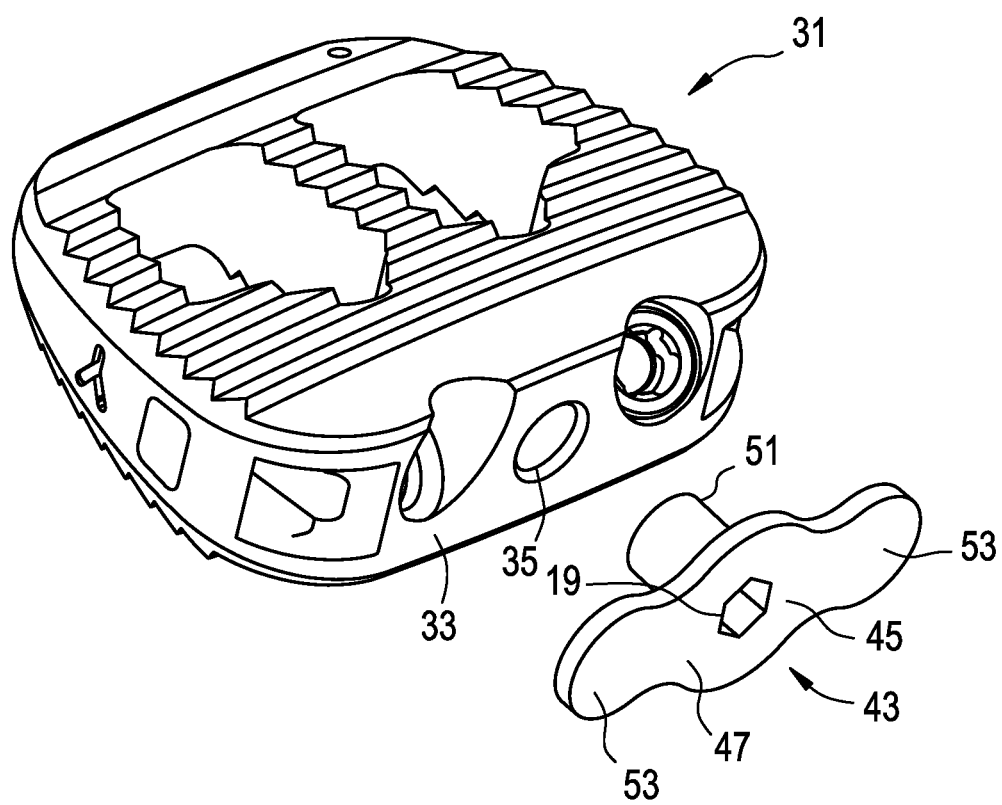
FIG. 5 discloses an exploded version of a fourth embodiment of the present invention (without screws) having a smooth post and lateral flanges.

The purpose of the flange is to provide a physical stop against the anterior movement of a screw expulsing from the cage. Because the flanges do not enter the bone, they need not have sharp features. In fact, because the implanted flanges are likely located near the aorta or vena cava of the patient's vascular system, it is preferred that the flanges consist of only smooth edges and surfaces. For example, FIG. 4 shows a pair of flanges that have only smooth surfaces.

Any feature that effectively penetrates the bone and locks the cover plate into an adjacent vertebral body can be considered a bone-securing feature. In some embodiments (as in FIG. 1A), the bone-securing feature 15 is a tooth, while in others (as in FIG. 6), it is a knife-edge 203.

In some embodiments using cover plate rotation for bone securement, the tooth extends transversely from the longitudinal axis of the base portion of the cover plate and in the same plane as the base portion, as in FIG. 1A. In some embodiments using cover plate tapping for bone securement, the knife-edge extends perpendicularly from the longitudinal axis of the base portion of the cover plate but normal to the plane of the base portion, as in FIG. 6.

In some preferred embodiments, the bone-securing feature enters the bone by first placing the post of the cover plate into the corresponding cage receptacle so that the bone securement feature is against the anterior face of a vertebral body and simply tapping the base portion of the cover plate in a posterior direction until the cover plate contacts the anterior wall of the cage. In other embodiments, the cover plate need not contact the anterior wall of the cage. This method may be used for the securement of the assembly of FIG. 6.

In other embodiments, the bone-securing feature enters the bone by first placing the post of the cover plate into the corresponding cage receptacle so that each bone securement feature is between the endplates of opposed vertebral bodies, and then rotating the cover plate until the cover plate contacts the anterior wall of the cage. This method may be used for securement of the assembly of FIG. 1A.

Now referring to FIGS. 4A-C, 5 and 7, there is provided an assembly comprising:
a) an intervertebral fusion cage 31 positionable between adjacent vertebral bodies, the cage having an anterior face 33 having a receptacle 35 and a pair of anchor holes 37,
b) bone anchors 38 received in the anchor holes, each anchor having a proximal head 40, and
c) a cover plate 43 having:
   i) a base portion 45 having an anterior face 47 and a posterior face (not shown),
   ii) a post 51 extending from the posterior face of the base portion and removably engaged in the receptacle of the cage, and
   iii) opposed flanges 53 extending from the base portion, each flange located substantially anterior to a respective anchor head to prevent backout of the associated anchor.

In some embodiments, the cover plate further comprises:
   iv) opposed bone-securing features 55 extending from the base portion, as in FIG. 7.

Figure 8:
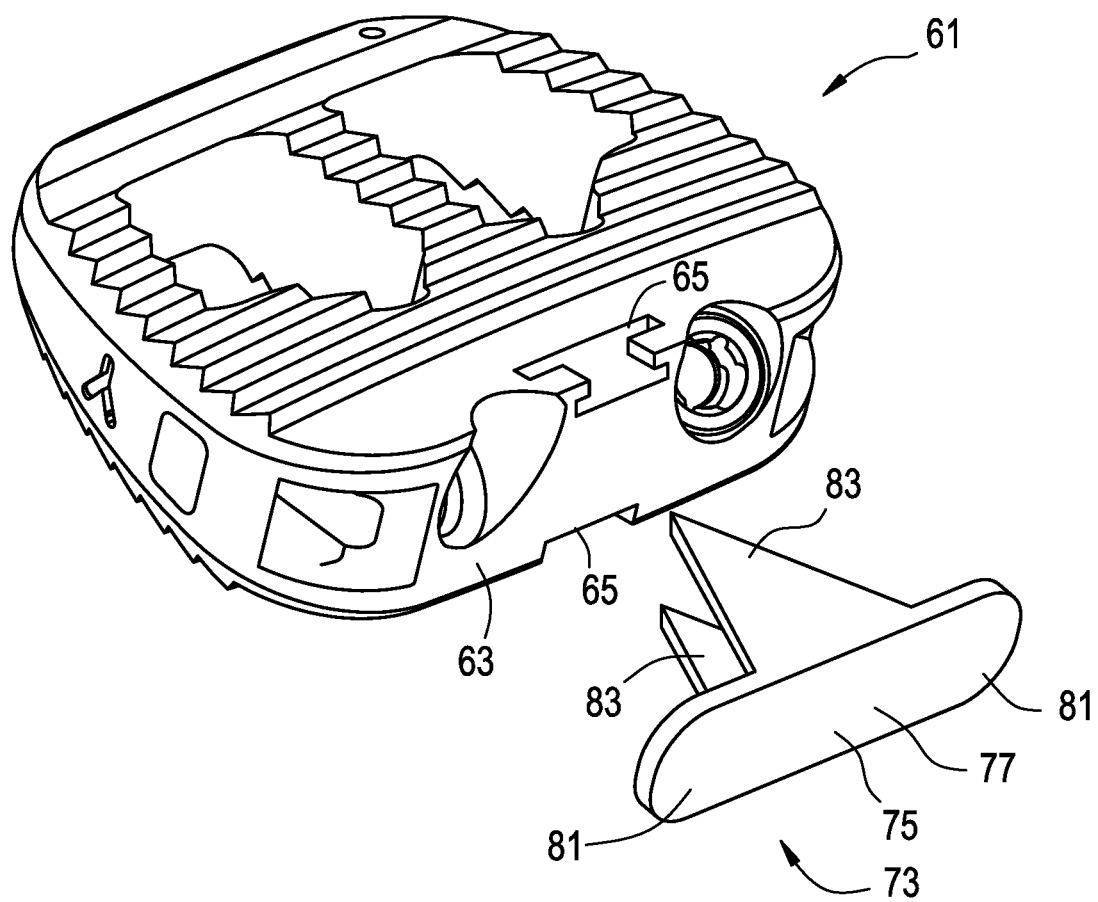
FIG. 8 discloses an exploded version of a seventh embodiment of the present invention (without screws) having opposed bone-securing features and lateral flanges.

Now referring to FIG. 8, there is provided an assembly comprising:
a) an intervertebral fusion cage 61 positionable between adjacent vertebral bodies, the cage having an anterior face 63 having a pair of slots 65 and a pair of anchor holes 67,
b) bone anchors (not shown) received in the screw holes, each anchor having a proximal head,
c) a cover plate 73 having:
   i) a base portion 75 having an anterior face 77 and a posterior face (not shown), ii) opposed flanges 81 extending laterally from the base portion, each flange located substantially anterior to a respective anchor head to prevent backout of the respective anchor head, iii) opposed bone-securing features 83 extending from the base portion and passing through the respective slots.

Figure 9:
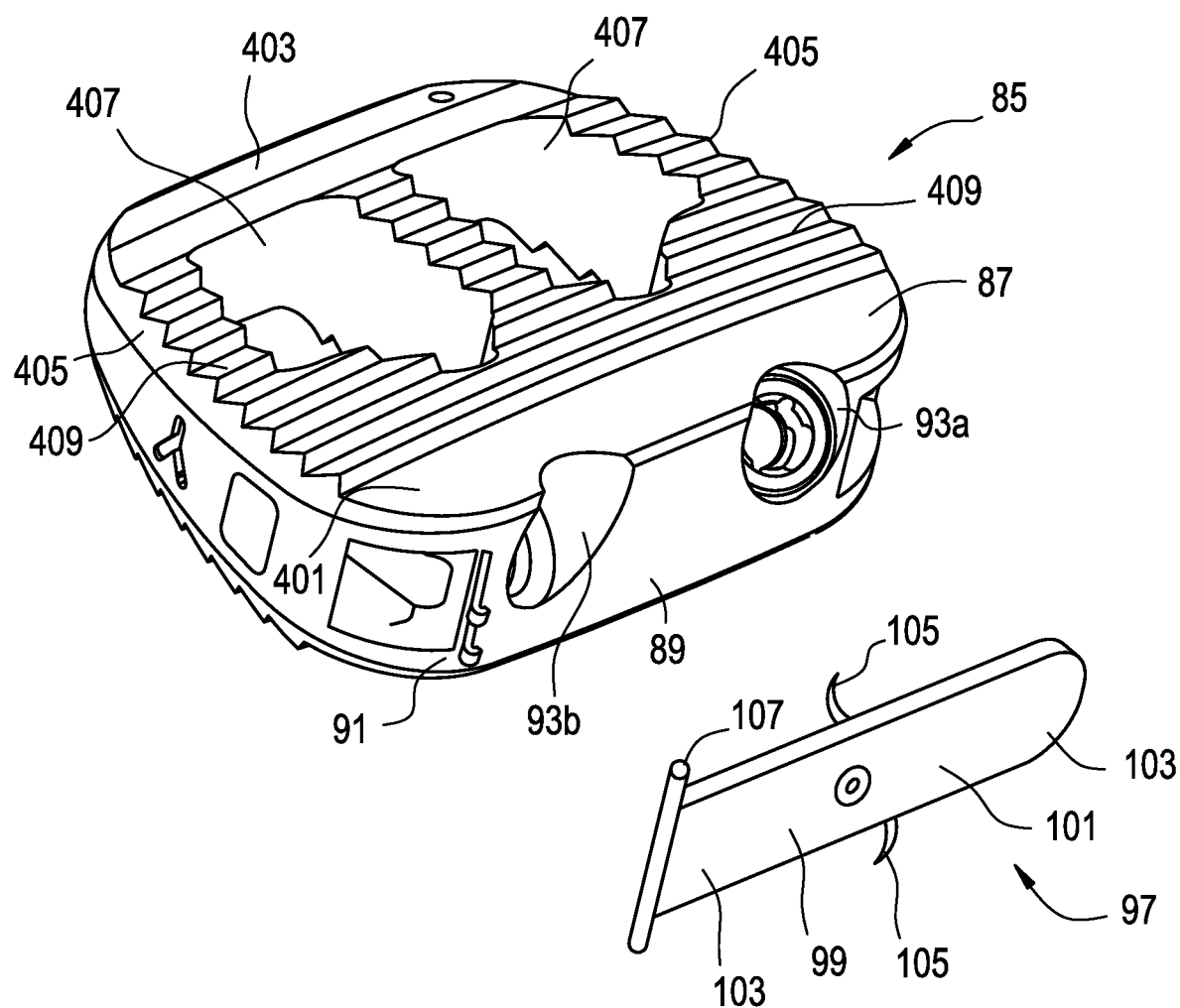
FIG. 9 discloses an exploded version of an eighth embodiment of the present invention (without screws) having bone-securing features and lateral hooks.

Now referring to FIG. 9, there is provided an assembly comprising:

a) an intervertebral fusion cage 85 positionable between adjacent vertebral bodies, the cage having an anterior wall 87 having an anterior face 89, the anterior face having a pair of pivoting features (preferably hooks 91 extending therefrom) and a pair of anchor holes 93 extending therethrough, b) bone anchors 95 received in the anchor holes, each anchor having a proximal head, c) a cover plate 97 having:

i) a base portion 99 having an anterior face 101 and a posterior face (not shown), ii) opposed flanges 103 extending laterally from the base portion, each flange located substantially anterior to a respective screw head to prevent backout of the respective anchor head, iii) opposed bone-securing features 105 rotatably connected to the base portion, iv) a bar 107 extending from the base portion and received in the hooks.

Figure 10:
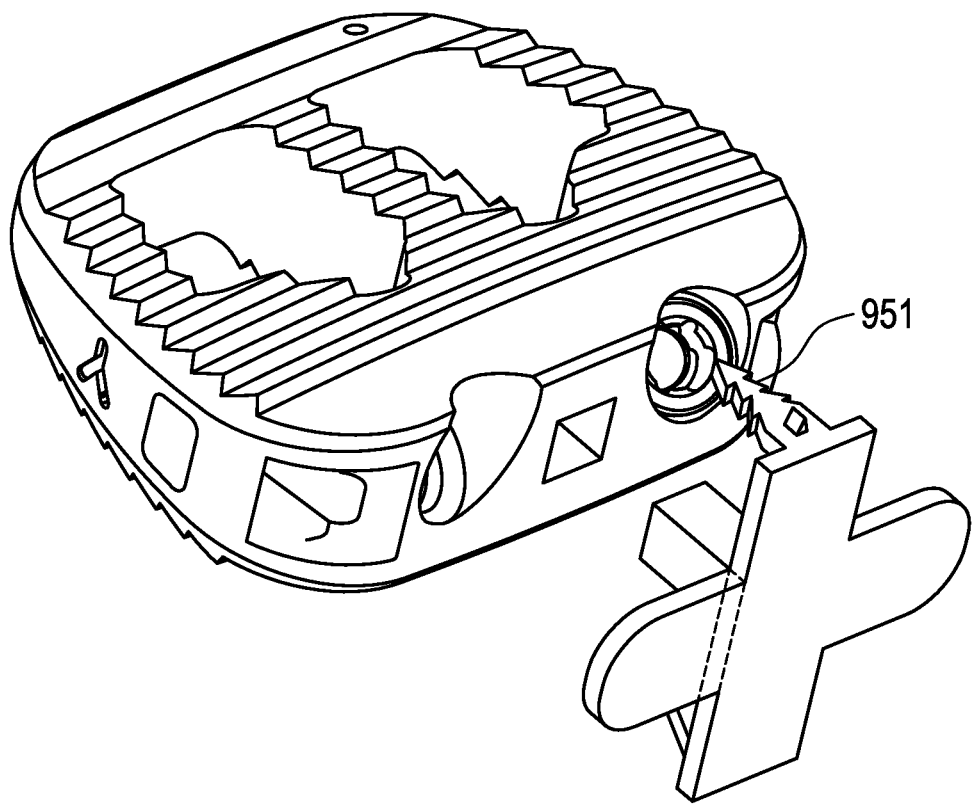
FIG. 10 discloses a cover plate in which the bone-securing features comprise barbs that provide both ease of insertion and expulsion resistance.

In some embodiments, the secondary cover plate may include features that promote ease of insertion, but would also strongly resist expulsion forces. For example, FIG. 10 discloses a cover plate in which the bone-securing features comprise barbs 951 that provide both ease of insertion and expulsion resistance. Likewise, FIGS. 6 and 7 each disclose a bone engaging feature 801 on a surface of a knife-edge, wherein the tooth extends perpendicularly to the longitudinal axis of the knife-edge. The bone engaging feature can be a tooth (as shown), a pyramid, a ridge, a keel, or a spike. This tooth provides both ease of insertion and expulsion resistance.

In addition to the anti-backout features that could be designed into the secondary cover plate, a combination of one or more of the following features could also be introduced to enhance performance: bone growth coatings (i.e., titanium calcium, phosphate, or hydroxyapatite; porous features in the bone-securing portions; anti-infection coatings; and tissue anti-adhesion coatings.

In the embodiments shown (as in FIG. 1A), the advancement of the cover plate is coupled with rotation of the cover plate. However, in other embodiments (not shown), the advancement of the cover plate is de-coupled from rotation of the cover plate. This may be accomplished by making the cover plate from two different components having separate drive features.

In general, the cage of the present invention is a stand-alone cage adapted for use in intervertebral fusions. These cages typically have screw holes through the anterior face for receiving bone screws. In some embodiments, and now referring to FIG. 9, the cage of the present invention comprises:

a) an anterior wall 87 having an anterior surface 89, an upper surface 401, a lower surface (not shown), a first throughhole 93a extending upwards from the anterior surface and a second throughhole 93b extending downwards from the anterior surface, b) a posterior wall 403, and c) first and second side walls 405 connecting the anterior and posterior walls.

Typically, the anterior, posterior and sidewalls of the cage define a central, vertical through-hole 407 that is adapted for promoting fusion between opposed vertebral bodies. Typically the sidewalls of such cages further comprise at least one throughhole to promote bone in-growth. Typically, the upper and lower surfaces of the cage have teeth or ridges 409 for rigidly gripping the opposed vertebral bodies. The posterior wall may have a tapered posterior surface adapted to ease insertion of the cage into the disc space. Generally, the cage may be used in either the lumbar, thoracic or cervical portions of the spine.

The bone anchors of the present invention are generally bone screws.

In one method of using the present invention, the cover plate is intended to be inserted/driven perpendicular to the proximal face of the cage in-line with the inserter. It is either delivered through a separate device or through a multipurpose inserter that delivers the cage and then selectively allows the user to engage the cover plate. After the cage is placed and positioned per surgeon preference, a cover plate could be inserted up against a proximal face of the cage and deployed. As taught, the plate or portions of the plate penetrates the adjacent vertebral bodies either through the anterior face or from within or partially within the disc space.

In general, the cover plate, cage and bone anchors are made from metallic materials, ceramic or polymeric materials.

If a metal is chosen as the material of construction, then the metal is preferably selected from the group consisting of nitinol, titanium, titanium alloys (such as Ti-6A1-4V), chrome alloys (such as CrCo or Cr—Co—Mo) and stainless steel.

If a polymer is chosen as a material of construction, then the polymer is preferably selected from the group consisting of polycarbonates, polyesters, (particularly aromatic esters such as polyalkylene terephthalates, polyamides; polyalkenes; poly(vinyl fluoride); PTFE; polyarylethyl ketone PAEK; and mixtures thereof.

In some embodiments, the bone screws are made of a stainless steel alloy, preferably BioDur® CCM Plus® Alloy available from Carpenter Specialty Alloys, Carpenter Technology Corporation of Wyomissing, Pa. In some embodiments, the cage is made from a composite comprising carbon fiber. Composites comprising carbon fiber are advantageous in that they typically have a strength and stiffness that is superior to neat polymer materials such as a polyarylethyl ketone PAEK. In some embodiments, the cage is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the cage is made from a neat polymer without any carbon fiber additive. Preferably, the polymer is a polyarylethyl ketone (PAEK), more preferably PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

I claim:

1. An assembly comprising:
a) an intervertebral fusion cage positionable between adjacent vertebral bodies, the cage having an anterior face having a pair of upper and lower slots and a pair of anchor holes,
b) bone anchors received in the anchor holes, each anchor having a proximal head,
c) a cover plate having:
   i) a base portion having an anterior face and a posterior face,
   ii) opposed flanges extending laterally from the base portion, each flange located substantially anterior to a respective anchor head to prevent backout of the respective anchor head,
   iii) opposed upper and lower bone-securing features extending from the base portion and passing through the respective slots,
   wherein the flanges are distinct from the bone-securing features, and wherein the bone-securing features pass through the slots and out of the cage.

* * * * *